(12) United States Patent
Demir et al.

(10) Patent No.: US 9,326,728 B2
(45) Date of Patent: May 3, 2016

(54) BIOMEMS SENSOR AND APPARATUSES AND METHODS THEREFOR

(75) Inventors: Hilmi Volkan Demir, Ankara (TR); Christian Matthew Puttlitz, Fort Collins, CO (US); Rohat Melik, Ankara (TR)

(73) Assignee: INNOVATIVE IN VIVO SENSING, LLC, Fort Collins, CO (US)

( * ) Notice: Subject to any disclaimer, the term of this patent is extended or adjusted under 35 U.S.C. 154(b) by 725 days.

(21) Appl. No.: 13/035,662

(22) Filed: Feb. 25, 2011

(65) Prior Publication Data

US 2011/0152725 A1      Jun. 23, 2011

Related U.S. Application Data

(63) Continuation of application No. PCT/US2009/055772, filed on Sep. 2, 2009.

(60) Provisional application No. 61/187,548, filed on Jun. 16, 2009, provisional application No. 61/093,688, filed on Sep. 2, 2008.

(51) Int. Cl.
  *A61B 5/103* (2006.01)
  *A61B 5/117* (2006.01)
  *A61B 5/00* (2006.01)
  (Continued)

(52) U.S. Cl.
  CPC .............. *A61B 5/6846* (2013.01); *A61B 5/0031* (2013.01); *A61B 5/4504* (2013.01); *A61B 2562/02* (2013.01); *A61B 2562/0261* (2013.01); *A61B 2562/046* (2013.01);
  (Continued)

(58) Field of Classification Search
  CPC .. G01B 7/22; G01L 9/003; A61B 2562/0261; A61B 2562/0252
  USPC .............................................. 600/587; 73/780
  See application file for complete search history.

(56) References Cited

U.S. PATENT DOCUMENTS 7,181,975 B1 * 2/2007 Bradley et al. .................. 73/724
7,357,037 B2    4/2008 Hnat et al.
(Continued)

FOREIGN PATENT DOCUMENTS

DE     10 2005 045 739 A1    4/2007
DE     10 2006 051 173 A1    3/2008
(Continued)

OTHER PUBLICATIONS

PCT Demand Chapter II Under Article 34 submitted Feb. 2, 2010 issued in related PCT/US2009/055772.
(Continued)

*Primary Examiner* — Brian Szmal
*Assistant Examiner* — H. Q. Nguyen
(74) *Attorney, Agent, or Firm* — Rossi, Kimms & McDowell LLP

(57) ABSTRACT

Electronic devices, apparatus, systems, and methods of operating and constructing the devices, apparatus, and/or systems include a wireless sensor configured to measure strain of hardware implanted in a subject. In various embodiments, temporal measurement of the hardware strain includes monitoring changes of the resonant frequency of the sensor. The sensor can be realized as an inductively powered device that operates as an all-on-chip resonator, where the components of the sensor are biocompatible. Additional apparatus, systems, and methods are disclosed.

41 Claims, 37 Drawing Sheets

(51) Int. Cl.
  *H01F 41/04* (2006.01)
  *H01F 17/00* (2006.01)
(52) U.S. Cl.
  CPC ........ *H01F 41/042* (2013.01); *H01F 2017/006* (2013.01); *Y10T 29/49103* (2015.01)

(56) References Cited

U.S. PATENT DOCUMENTS

| | | | |
|---|---|---|---|
| 7,913,569 B2 * | 3/2011 | Girshovich et al. | ............ 73/779 |
| 8,070,695 B2 | 12/2011 | Gupta et al. | |
| 8,083,741 B2 | 12/2011 | Morgan et al. | |
| 8,104,358 B1 * | 1/2012 | Jia et al. | ............ 73/780 |
| 8,529,474 B2 | 9/2013 | Gupta et al. | |
| 2003/0139677 A1 | 7/2003 | Fonseca et al. | |
| 2004/0113790 A1 | 6/2004 | Hamel et al. | |
| 2006/0032314 A1 | 2/2006 | Hnat et al. | |
| 2008/0077016 A1 | 3/2008 | Sparks et al. | |
| 2008/0169883 A1 | 7/2008 | Hsu et al. | |
| 2012/0065548 A1 | 3/2012 | Morgan et al. | |
| 2014/0066814 A1 | 3/2014 | Gupta et al. | |

FOREIGN PATENT DOCUMENTS

| | | |
|---|---|---|
| JP | 06-307960 A | 11/1994 |
| JP | 10-335675 A | 12/1998 |
| JP | 2005-532123 A | 10/2005 |

OTHER PUBLICATIONS

Notification of Transmittal of the International Search Report and the Written Opinion of the International Searching Authority mailed Nov. 3, 2009 issued in related PCT/US2009/055772.
International Preliminary Report on Patentability (IPEA/409).
Corresponding Korean Office Action in 10-2011-7003823: Notice to File a Response issued Aug. 2, 2012.
Corresponding Chinese Office Action in 200980132226.4: First Office Action issued Aug. 13, 2012 (English Translation Only).
Notification of Reasons for Refusal for corresponding JP 2011-525295, mail date Jan. 27, 2014. English translation provided.
Canadian Office Action dated Apr. 11, 2013 in corresponding Canadian Application No. 2,734,690.
European Office Action dated May 6, 2013 in corresponding European Application No. 09 792 188.6-1657.
European Office Action dated May 28, 2014 in corresponding European Application No. 09 792 188.6-1657.
Bio-Implantable Passibe On-Chip RF-MEMS Strain Sensing Resonators for Orthopaedic Applications, Journal of Micromechanical and Microengineering, Rohat Melik, Nihan Kosku Perkgoz, Ernie Unal, Christian Puttlitz, and Hilmi Volkan Demir, published Oct. 7, 2008.
Canadian Office Action dated Jul. 29, 2014 in corresponding Canadian Application No. 2734690.
Full English Translation of DE 10 2005 045 739 A1 previously cited.
Extended European Search Report issued in EP15186883.3, mailed Feb. 24, 2016.

* cited by examiner

DETERMINE A SHIFT IN A RESONANT FREQUENCY OF A SENSOR DISPOSED ON IMPLANTABLE HARDWARE
↳110

DETERMINE TEMPORAL CHANGES IN STRAIN OF THE HARDWARE BASED ON THE DETERMINED SHIFT
↳120

*FIG. 1*

DETERMINE A RESONANT FREQUENCY OF A SENSOR, WHERE THE SENSOR IS DISPOSED ON HARDWARE IMPLANTED IN A SUBJECT
↳210

DETERMINE A SHIFT IN RESONANT FREQUENCY OF THE SENSOR BASED ON WIRELESS SIGNALS FROM THE SENSOR, WHERE THE WIRELESS SIGNALS ARE GENERATED FROM THE SENSOR IN RESPONSE TO ELECTROMAGNETIC FIELDS APPLIED TO THE SENSOR OVER A PERIOD OF TIME
↳220

DETERMINE A TEMPORAL CHANGE IN STRAIN OF THE HARDWARE, BASED ON THE SHIFT IN RESONANT FREQUENCY
↳230

*FIG. 2*

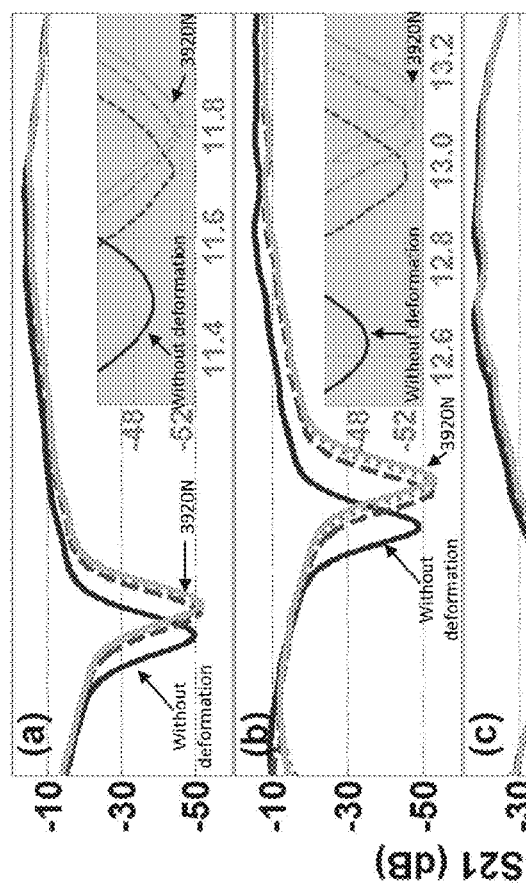
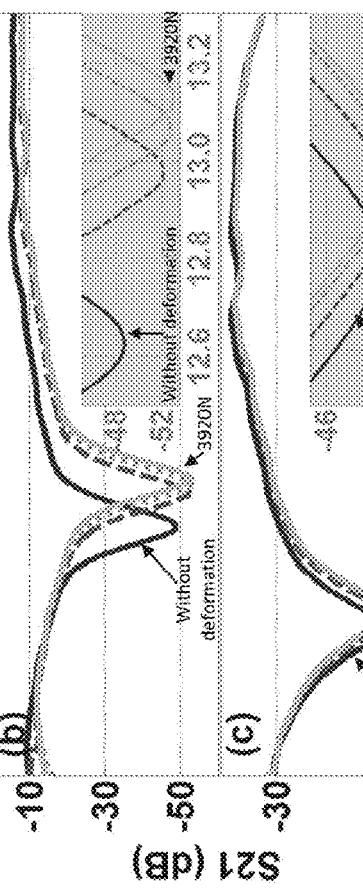
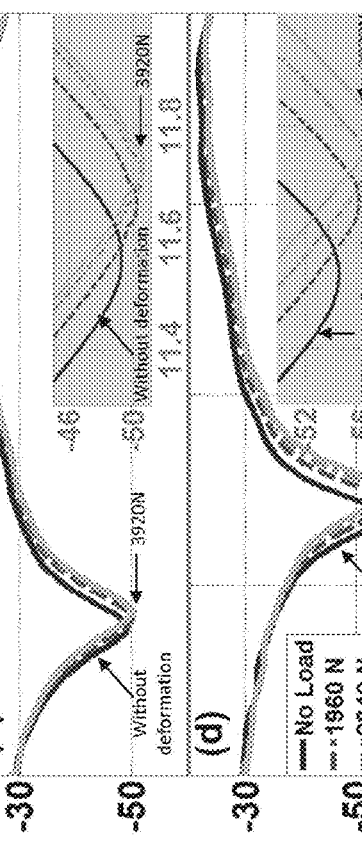
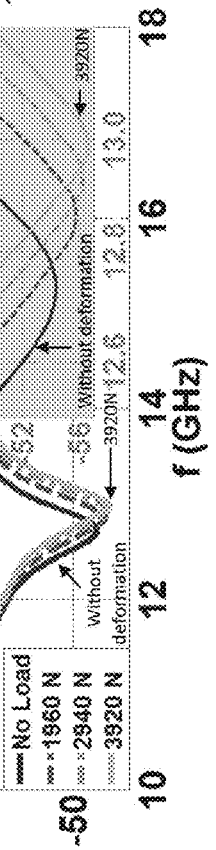
FIG. 52
FIG. 53
FIG. 54
FIG. 55

BIOMEMS SENSOR AND APPARATUSES AND METHODS THEREFOR

CROSS REFERENCE

This is a continuation of International Application PCT/US2009/055772 (published as WO 2010/028077 in English) having an international filing date of 2 Sep. 2009, which International Application claims the priority benefit of U.S. Provisional Patent Application Ser. No. 61/187,548 filed 16 Jun. 2009 and of U.S. Provisional Patent Application Ser. No. 61/093,688 filed 2 Sep. 2008. The disclosures of the International Application and its priority applications, in their entirety, including the drawings, claims, and specification thereof, are incorporated herein by reference.

BACKGROUND

Orthopaedic extremity injuries present a large medical and financial burden to both the United States and worldwide communities. Approximately 8 million bone fractures are reported per annum in the United States, and about 10% of these fractures do not heal properly. For injuries that involve a significant disturbance to the vascular supply, the rates of aberrant bone healing are nearly 50%. The most common complication is bony non-union. These non-unions can be very costly because of both the direct cost to revise as well as associated costs such as lost productivity due to absence from work. It has been estimated that these costs can be reduced by at least 50% if complications associated within the early healing can be avoided or addressed.

The most common treatment for non-unions is additional surgery. The clinical outcome of these procedures is negatively correlated to the time between the initial surgery and the second surgery due to the temporal course of fibrous tissue accumulation at the fracture site. Thus, there is a crucial clinical need to determine the course of bone healing (aberrant versus normal) in the vitally important early stages of fracture site treatment and management. Current strategies that utilize injections of osseous "biologic" therapeutics, bone morphogenetic proteins (BMPs) or other growth factors that potentiate the osteoinductive activities of BMPs, have been proposed for non-invasively treating bony non-unions in the early healing phase. However, the ability to diagnose if adjunctive biologic treatments are necessary is not currently available.

Though the exact mechanism through which the bone healing sequence becomes impaired is poorly understood, many of these non-unions or pseudoarthroses (fibrous unions) result when there is a fracture condition that does not proceed through a stabilized, direct bony bridging (intramembranous ossification) healing pathway. Currently, clinicians usually monitor healing visually by radiographs, and may examine the mechanical condition of the union via manually bending the bone at the fracture. Unfortunately, the course of aberrant fracture healing is not easily diagnosed in the early time period when standard radiographic information of the fracture site is not capable of discriminating the healing pathway due to the relative paucity of mineralized tissue. Manual assessment of fracture healing is also inadequate as a diagnostic tool in the early stages of healing. Therefore, there is a need for new technologies that provide diagnostic information as to the course of healing within the first 6 post-operative weeks, which would provide a significant impact on the clinical orthopaedic practice and treatment of problematic fractures. The present invention addresses this need.

BRIEF DESCRIPTION OF THE DRAWINGS

Embodiments of the invention are illustrated by way of example and not limitation in the Figs. of the following accompanying drawings.

FIG. 1 illustrates features of an embodiment of a method for monitoring changes in a hardware device implanted in a subject.

FIG. 2 illustrates features of an embodiment of a method for monitoring changes in a hardware device implanted in a subject.

FIGS. 52-55 show experimental results comparing rectangular and circular geometries.

DETAILED DESCRIPTION

Figure 3:
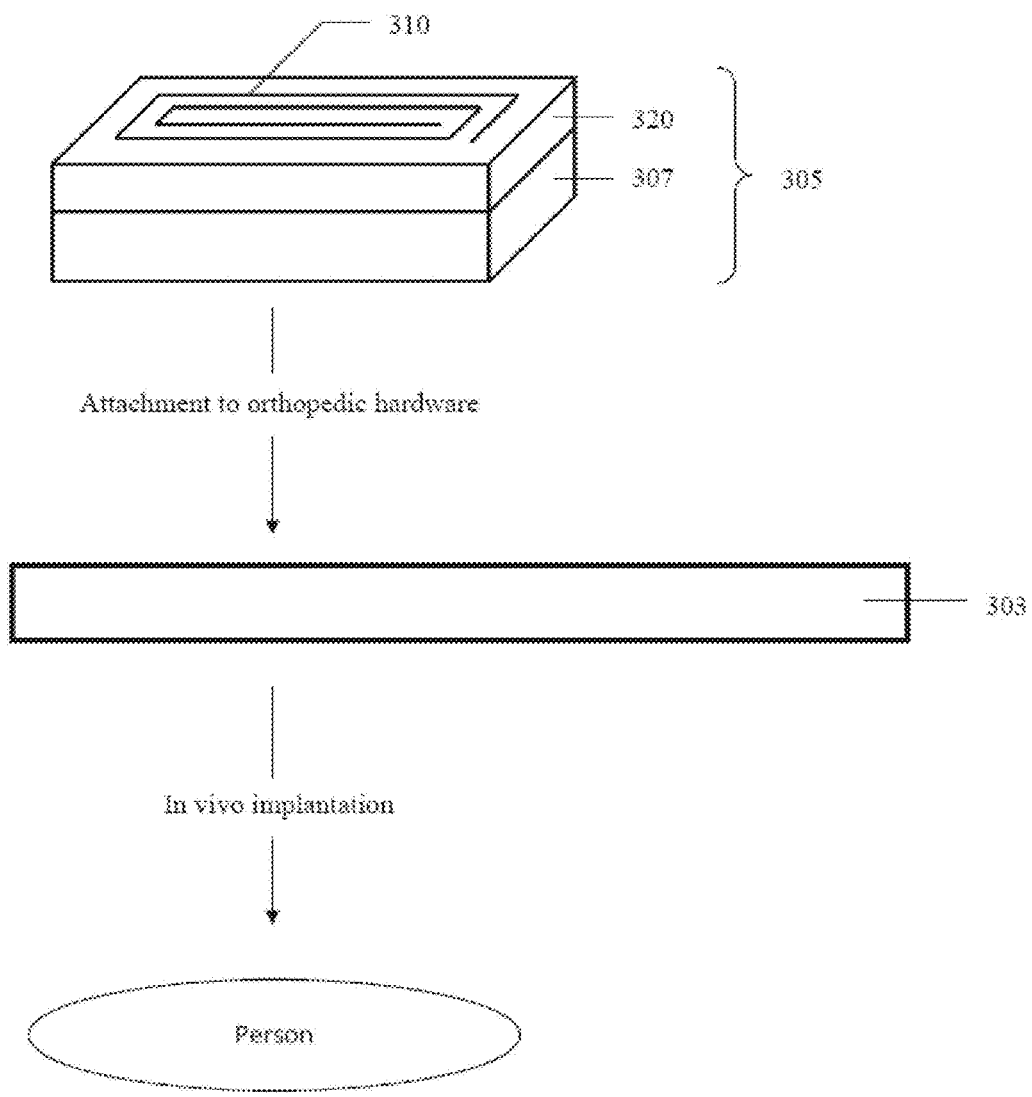
FIG. 3 illustrates features of an embodiment of a wireless sensor attachable to a hardware device for implantation in a biological subject.

The present disclosure relates generally to sensors and uses thereof, more particularly, to implantable sensors. The following detailed description refers to the accompanying drawings that show, by way of illustration, various embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, a wireless sensor is configured to measure strain of a hardware device implanted in a biological subject, which can include human and animal. Temporal measurement of the hardware strain can be conducted using measurements that include monitoring changes of the resonant frequency of the sensor. The sensor can be realized as an inductively powered device that operates as an all-on-chip resonator, where the components of the sensor are biocompatible. Such a sensor can be operated with a variety of electronic devices, apparatus, and systems.

It has been shown in clinical practice and via animal models that healing is critically-related to the degree of fracture stability and implant loading in the early time period. Animal studies using wired strain gages have demonstrated that the healing callus and bone assume an increasing proportion of the load as fracture healing proceeds, reducing the burden on the implanted hardware. If the course of the healing is aberrant, this gradual transfer of the loading burden is altered or non-existent, i.e., the healing tissue cannot assume its normal share of the load because it does not have the structural or material capacity to do so. In various embodiments, a telemetry system having a biocompatible, implantable sensor leverages the relationships between implant strain and bone healing as a function of the healing pathway.

To date, many of the technologies that seek to exploit the bone-implant load sharing phenomena have been considered too large in dimension or involve implantation of an associated power supply. Previous investigations have been successful in determining forces in the hip, spine, and shoulder. However, due to the relatively large size of the sensors and associated hardware (signal conditioning, modulation, etc.), most of the previous telemetry systems have been implanted inside of joint replacement components or bulky internal fixators. The result is that these devices have produced data that have been useful in the understanding of bone-implant loading, but such devices may not be appropriate for large-scale implementation as a diagnostic and/or prognostic tool. Also, due to the complexity of the designs and associated interconnectivity, manufacture of these systems is typically performed on a custom basis. The resulting expense may not justify their large scale manufacture.

In various embodiments, a radio frequency (RF) strain sensor design includes features using micro-electro-mechanical systems (MEMS) technology for implantation in a biological subject. The sensor can be mounted on implantable hardware for the implantation in the biological subject. The sensor can be structured to be inductively-powered, with no implantable power source. The sensor can be arranged on implanted hardware such that the sensor monitors the surface bending strains on the implanted hardware. The sensor can be arranged as a wireless sensor such that internal-to-external physical connections are not used to sense and transmit the in vivo biological data. Further, the miniaturization of such a device may allow for its use in applications that otherwise would not be possible. Such a bio-MEMs sensor can be arranged as a device that uses inductive power without incorporating a power supply, passively providing power, and has a physical size such that the bio-MEMS sensor alleviates many of the issues associated with currently conventional devices and associated methods. In addition, the structure of such bio-M EMS sensors allows for manufacture on a production scale that can be significantly more cost effective than manufacture of the currently conventional devices.

In various embodiments, a sensor essentially acts as a wireless strain gauge attached to the surface of a hardware device, namely an orthopaedic or neurosurgical device, such as a fracture fixation plate posterior spinal pedicle screw fixation system, spinal interbody fixation device, a vertebral body replacement device, intramedullary rod/nail, allograft fracture fixation or vertebral spacer, spinal motion preservation systems (such as intervertebral disc replacement and dynamic stabilization systems), and craniofacial fixation and distraction osteogenesis hardware systems, that is implantable in a subject. This configuration and operation is in contrast with many other wireless sensors that are used in the vascular system of a subject. The design of the bioMEMS sensor is such that straining the integrated circuit of the bioMEMS results in a shift in its resonant frequency. By detecting this frequency shift and implementing a pre-determined strain-frequency calibration, the temporal changes in hardware strain can be longitudinally monitored. The components of the sensing system can include an inductor or other means of applying electromagnetic fields, the implantable sensor, a receiving antenna. The implantable sensor can be also referred to as the "resonator" of the sensing system. The receiving antenna can be realized as a receiving antenna/spectrum analyzer apparatus. The inductor produces an alternating external magnetic field that induces an electric current in the sensor. The sensor has an associated resonance frequency that is uniquely related to the current configuration of the circuit formed of the sensor. The resonance frequency of the sensor changes as the sensor is deformed. Signals generated at the sensor, in response to the applied electromagnetic fields, can be received from the sensor at the attached antenna of the spectrum analyzer and can be used to determine the resonance frequency of the circuit formed by the sensor.

FIG. 1 illustrates features of an embodiment of a method for monitoring changes in hardware implanted in a subject. At 110, a shift in a resonant frequency of a sensor disposed on the hardware is determined. The sensor can be arranged as a biocompatible, inductively powered device. The resonant frequency of the sensor can be excited by subjecting the sensor to an alternating magnetic or electromagnetic field. At 120, temporal changes in strain of the hardware are determined based on the determined shift. The temporal changes can be determined by analyzing signals from the sensor, where the signals are generated from the sensor in response to subjecting the sensor to the alternating magnetic or electromagnetic field. In various embodiments, the shift in resonant frequency is used without using the absolute values of the resonant frequencies with respect to determining the temporal changes in strain of the hardware. Based on the temporal changes in strain of the hardware, changes in the subject can be determined.

FIG. 2 illustrates features of an embodiment of a method for monitoring changes in hardware implanted in a subject, such as a biological subject. At 210, a resonant frequency of a sensor is determined where the sensor is disposed on the hardware implanted in the subject. The sensor can be being inductively powered by an electromagnetic field such that, with respect to power, the sensor operates as a contact-less device without an incorporated power supply. The sensor can be attached to the surface of a hardware device that is implantable in a subject.

At 220, a shift in resonant frequency of the sensor is determined based on wireless signals from the sensor, where the wireless signals are generated from the sensor in response to electromagnetic fields applied at different times. These electromagnetic fields act as probes for read-out of the sensor configured as a way of determining strain on the implanted hardware device. In various embodiments, the shift in resonant frequency can be determined from the signals from the sensor without considering the energizing signal used to power the sensor.

At 230, temporal changes in strain of the hardware are determined, based on the shift in resonant frequency. Temporal changes in strain of the hardware device can be determined by implementing a strain-frequency calibration of the hardware. The temporal changes in strain of the hardware can be determined from monitoring surface strains of the hardware device. Changes in the biological subject can be determined based on the temporal changes in strain of the hardware device. For a fracture fixation plate implanted in a person, these changes can be monitored to be used in the diagnosis and the prognosis for the healing of the bone fractured in the person. For a spinal fixation device, these changes can be used to determine the course of fusion progression.

FIG. 3 illustrates features of an embodiment of a wireless sensor 305 attachable to hardware 303 for implantation in a biological subject. Sensor 305 includes a substrate 307, a dielectric material 320 disposed on substrate 307, and a conductive coil 310 disposed on dielectric material 320 such that dielectric material 320 and conductive coil 310 are arranged as a resonator. Substrate 307 can also be arranged as part of the resonator. Substrate 307, dielectric material 320, and conductive coil 310 are structured as a biocompatible, inductively powered device attachable to hardware 303 for implantation in a biological subject. The response of sensor 305 inserted in soft tissue may be linear with respect to applied force over a wide range of forces.

Dielectric material 320 can be solid material that includes biocompatible electrically insulating material. Dielectric material 320 can include, but is not limited to, silicon nitride. Conductive coil 310 includes biocompatible electrically conductive material. Conductive coil 310 can include, but is not limited to, gold. Conductive coil 310 can be arranged as an inductor and part of a capacitor that forms a resonator, where dielectric material 320 forms part of the capacitor. Substrate 307 can function as an effective plate of the capacitor with conductive coil 310 forming the other plate and with dielectric 320 between and contacting conductive coil 310 and substrate 307. Alternatively, one or more conductive materials can be used as part of the capacitor. For example, a conductive layer can be disposed between substrate 307 and dielectric material 320. A conductive layer can be disposed between coil 310 and dielectric 320.

In various embodiments, the resonator function of the sensor is conducted by a coil, such as conductive coil 310 of FIG. 3, providing inductance, and the on-chip capacitance provided by dielectric material 320. This configuration allows for tuning of the sensor by the dielectric film rather than using external capacitors that may undesirably increase the effective device area and decrease the resonator "Q-factor," which is the ratio of the stored energy to the lost energy for a circuit or device. For sensor 305, structural arrangements for the conductive coil and dielectric material, along with choice of materials, can be used to design towards a maximum quality factor with minimum circuit spacing. An example embodiment includes a spiral geometry for a conductor coil implemented as an all-on-chip resonator based on Q-factor considerations. For example, the chip with the spiral geometry can be formed with a chip size of about 500 square microns with a Q-factor of nearly 50 operating at a resonance frequency of about 7 GHz. A Q-factor of about 50 may be configured as a high Q-factor, which can enhance operation of sensor 305 as a wireless sensor attached to hardware to function essentially as a strain gauge. Structures based on spiral-coil inductors for a coil can be used to realize the reduced area for coil on a chip, while increasing the Q-factor.

In various embodiments, an on-chip resonator can be realized without a cavity on the chip. In such a sensor, a self-tuning spiral-coil based architecture is used without a cavity on the chip using improved design parameters at a higher operating frequency. For example, using an on-chip resonator on silicon, the Q-factor can be raised to more than 90 for a chip size of less than 200 square microns. Thus, significantly small-size and high-Q resonators can be achieved in comparison with convention resonators using external tuning capacitors and/or a cavity in a chip. Greater increases in the Q-factor can be attained by using a suspended architecture, which is obtained by removing (etching) silicon under the sensor. When two sensors are compared, where all of the resonator features are of equal dimension, but one's substrate is etched (suspended architecture) and the other is not (planar architecture), the suspended device demonstrates a 10% increase in Q-factor over the planar device.

The strain sensor can be configured to produce a resonance frequency shift that is sufficiently large so that small changes in strain can be detected by the sensor. Such a resonance frequency shift can be attained with isotropic circular strain sensor resonators that allow for higher Q-factors with smaller spacing compared to rectangular designs. The circular architecture enables a significantly higher resonance frequency shift, for example 500 MHz as opposed to 330 MHz, and higher sensitivity because of its isotropic geometry. This architecture can result in a substantial improvement in the performance of these resonators for use as bio-implant strain sensors.

In various embodiments, wireless inductively, powered strain sensors can be realized using architectures that provide effective metamaterial properties. A metamaterial affects electromagnetic waves by having structural features smaller than the wavelength of electromagnetic radiation with which it interacts. By using a split-ring-resonator (SRR) structure as a metamaterial for the sensor, the sensor can obtain high Q-factors, high transmission dips on resonance, high resonance frequency shifts, high sensitivities, and very good linearity, which are appropriate properties for an accurate wireless sensor. Furthermore, the sensor achieves significantly lower resonance frequencies (50 Mhz to 1 GHz) with sharper dips, which is useful for sensing applications involving soft tissue attenuation issues that can be associated with a biological subject. The strain readouts from the wireless sensor, which are obtained telemetrically, are found to be comparable to those obtained using commercially-available wired strain sensors that are used in electrical contact applications.

Various architectures for the conductive coil of the wireless sensor device can be used. In an example embodiment, multiple split-ring-resonators are incorporated into a compact nested architecture to lower the operating frequency of the sensor. This nested SRR sensor can outperform a non-nested SRR sensor in terms of sensitivity. This enhancement of sensitivity may be due to the occurrence of more gaps in the nested SRR as compared to the non-nested SRR.

In various embodiments, the substrate of the sensor may be a flexible substrate. A example of a flexible substrate is vacuum tape. Using a flexible substrate can make the wireless sensor more sensitive and linear compared to using a silicon substrate. A tape-based flexible metamaterial sensor can exhibit a significantly improved sensitivity level with a substantially reduced nonlinearity-error, in comparison to a silicon-based sensor of the same geometry.

Figure 4:
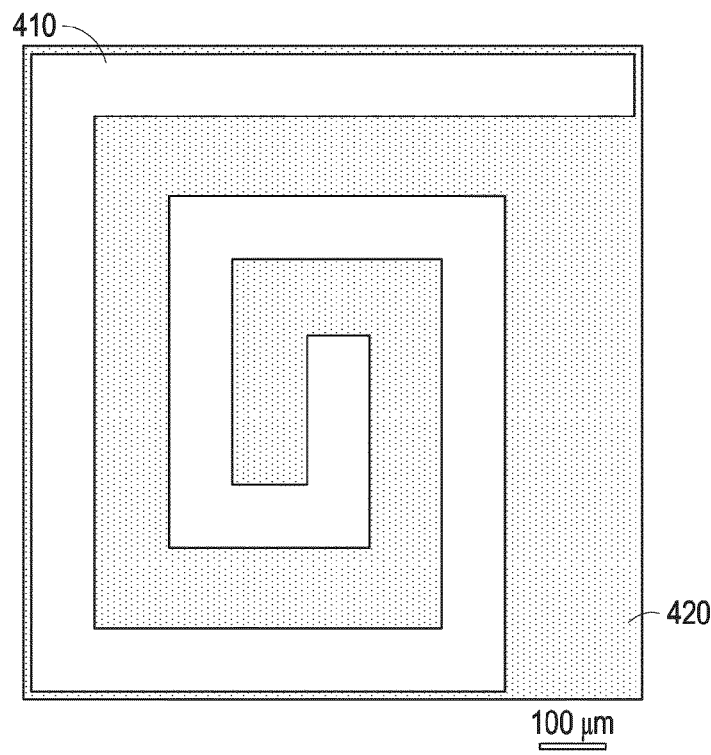
FIG. 4 shows an embodiment of a coil on a dielectric for a resonator.

A coil for an inductively coupled sensor can be structured according to various embodiments. FIG. 4 shows an embodiment of a coil 410 on a dielectric material 420. Coil 410 and dielectric material 420 can be composed of biocompatible materials if the sensor is used for implantation in a person or animal. Such biocompatible materials include, but are not limited to, gold and silicon nitride. In an experiment, a bioMEMS sensor having the coil structure of FIG. 4 was attached to an implantable plate using hard epoxy to monitor the strain on the implantable plate in real time. The fixated device operates as a strain sensor to measure the strain on the implantable plate. The sensor was characterized, in a compression setup, with a minimum of 115 kgf and a maximum of 276 kgf in the range of 100-300 kgf load range applied by the setup. As the external load was increased from 115 kgf to 276 kgf, the resonance was observed to shift to larger frequencies. In the characterization, cast polyamide was used as the implantable plate, with a young modulus of 3.14 GPa. A sensitivity level of 0.306 MHz/kgf was obtained for the bioMEMS sensor using the coil of FIG. 4.

Figure 5:
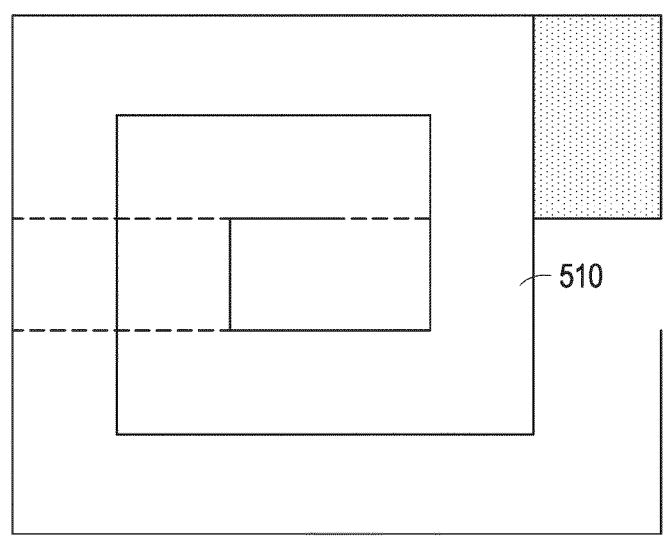
FIG. 5 shows an embodiment of a spiral coil for a resonator.

FIG. 5 shows an embodiment of a spiral coil 510. Spiral coil 510 can be arranged as a rectangular spiral coil that is a continuous coil with at least two turns. The square can have outer dimensions of 195×195 microns as an on-chip resonator. Such an on-chip resonator on silicon can operate at about 15 GHz with a Q-factor of 93.81. Other dimensions can be used. For example, a square with dimensions of 540×540 microns can have a resonant frequency ($f_0$) of 6.97 GHZ with a 3-dB bandwidth ($\Delta f$) of 148 MHz and Q-factor of 47.10. A square with dimensions of 520×520 microns can have a resonant frequency ($f_0$) of 7.12 GHZ with a 3-dB bandwidth ($\Delta f$) of 178 MHz and Q-factor of 38.48.

Figure 6:
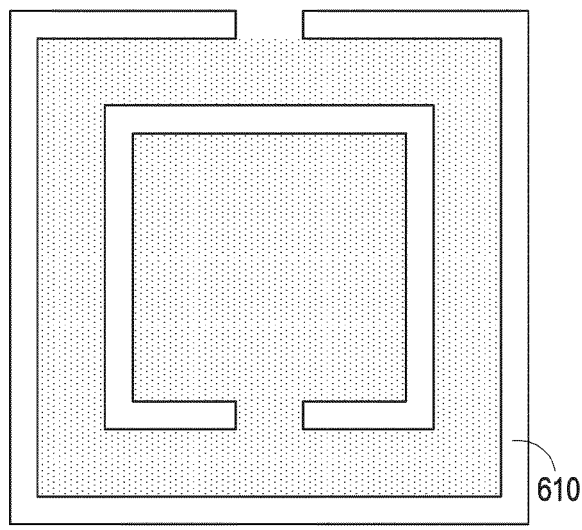
FIG. 6 shows an embodiment of a split ring resonator architecture.

FIG. 6 shows an embodiment of a split ring resonator architecture 610. Split ring resonator architecture 610 comprises a square inside a square. There is a gap in the outer square on one side and a gap in the inner square on the opposite side.

Figure 7:
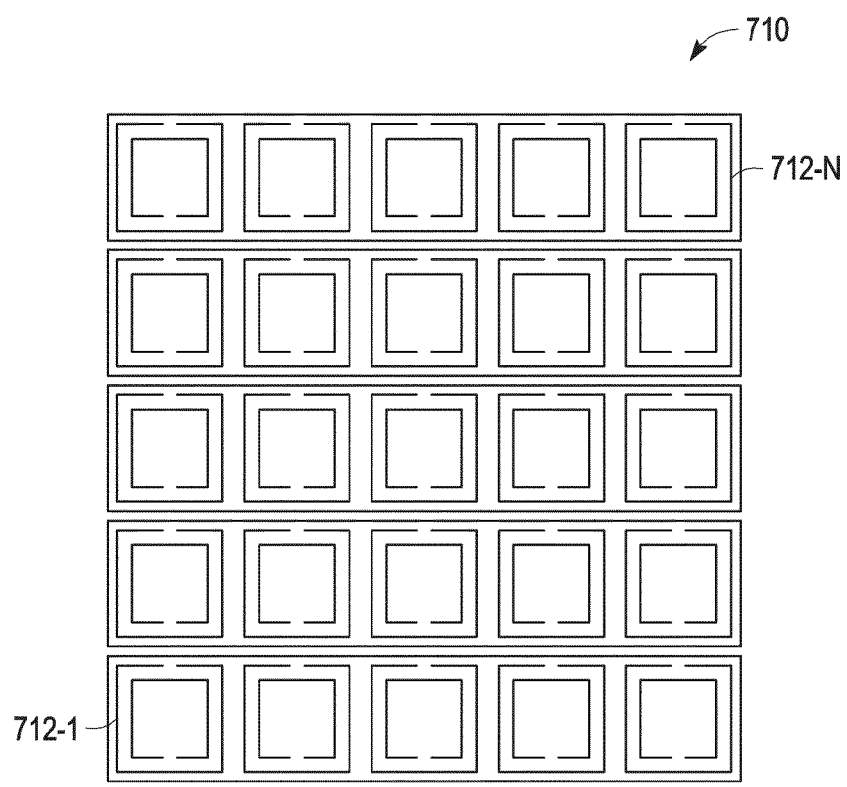
FIG. 7 shows an embodiment of a chip having an array of split ring resonators.

FIG. 7 shows an embodiment of a chip having an array 710 of split ring resonators 712-1 . . . 712-N. Each split ring resonator 712-1 . . . 712-N can comprise a square inside a square. Each split ring resonator 712-1 . . . 712-N can have an outer square that is 2.22 mm in length on each side and an inner square that is 1.5 mm in length on each side. Array 710 can be comprised of a 5×5 array of these squares as illustrated in FIG. 7. A 5×5 array SRR architecture can yield a sensitivity of 109 kHz/kgf (5.148 kHz/microstrain) with low nonlinearity-error of less than 200 microstrain. Array 710 can be realized as an N×N, where N is an integer other than 5.

Figure 8:
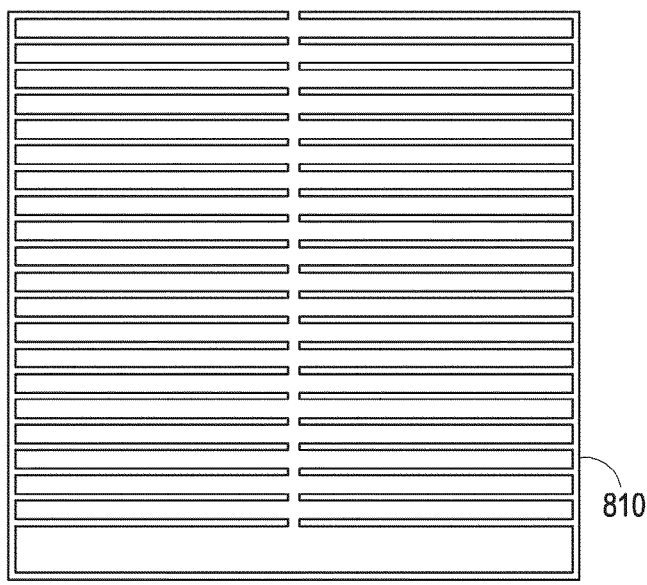
FIG. 8 shows an embodiment of a nested split ring resonator architecture.

FIG. 8 shows an embodiment of a nested SRR architecture 810. Nested SRR architecture 810 comprises many split ring resonators. In this embodiment, each SRR can have the same width and can share a common base, but the height of each one can be different. Also, the side opposite the base of each SRR can have a gap in it. Nested SRR architecture 810 can have a difference in height, from one resonator to the next resonator, of 0.8 mm where the base rectangle can be 1.8 mm tall. Nested SRR architecture 810 can be realized having other dimensions. In FIG. 8, nested SRR architecture 810 can have 20 turns. Nested SRR architecture 810 can have a structure with turns other than 20 turns.

Figure 9:
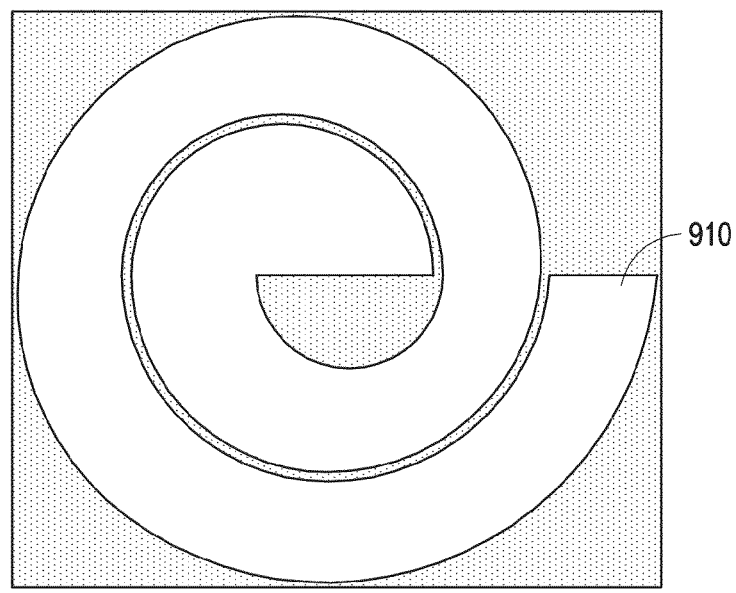
FIG. 9 shows an embodiment of a circular spiral coil resonator.

FIG. 9 shows an embodiment of a circular spiral coil resonator 910. Circular spiral coil resonator 910 can be a continuous coil, which can be formed with at least two spiral turns. It can be structured with a number of turns other than two turns. Circular spiral coil resonator 910 can have an outer diameter of 340 microns. It can have an outer diameter of a length other than 340 microns.

Figure 10:
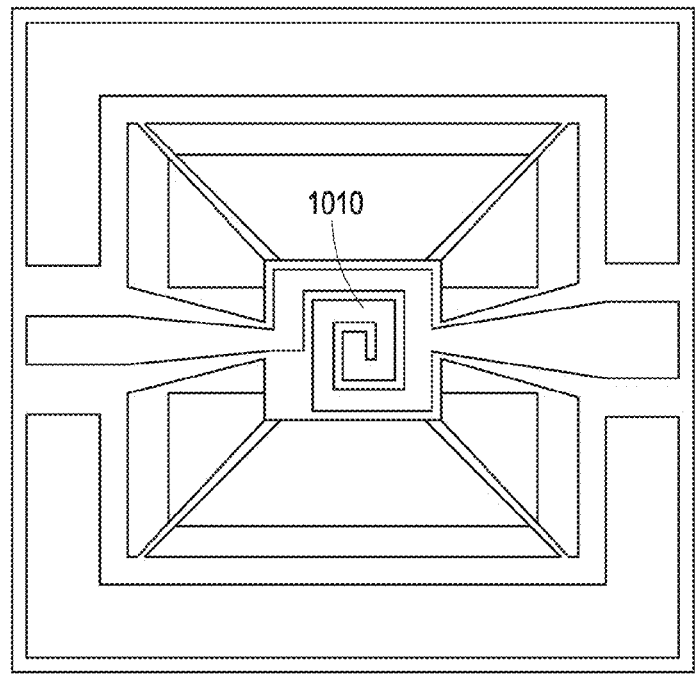
FIG. 10 shows an embodiment of an architecture in which a resonator is suspended.
Figure 11:
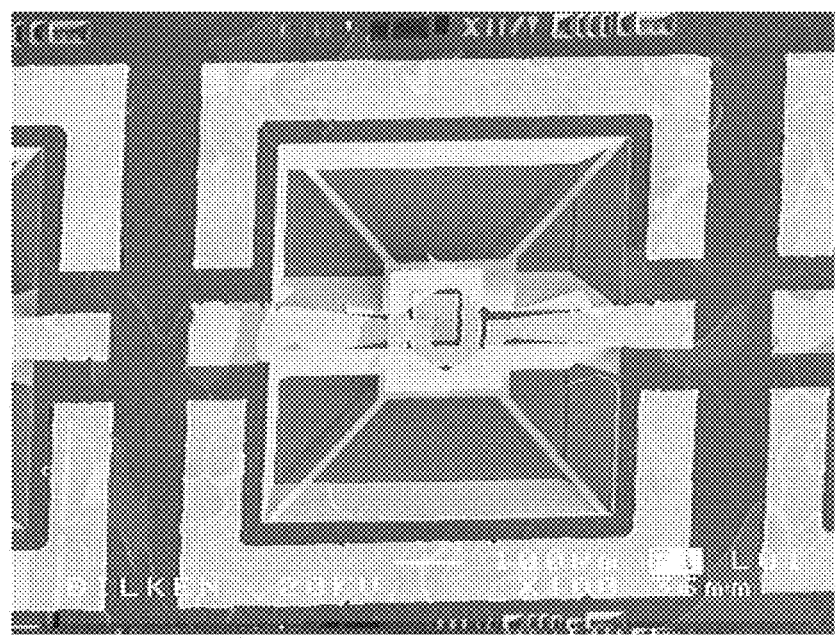
FIG. 11 shows a scanning electron microscope view of a single suspended resonator device.

FIG. 10 shows an embodiment of a architecture in which resonator 1010 is suspended. The suspended architecture can help increase the resonance frequency shift of resonator 1010. With a solid biocompatible substrate used to fabricate the chip, such as silicon, the substrate can be etched to obtain the suspended architecture. A single suspended device can be obtained by etching the substrate of a single planar device. When applying a load to both a single planar device and a single suspended device, the single suspended device can yield a higher resonance frequency shift and Q-factor than the single planar device. FIG. 11 shows a scanning electron microscope (SEM) view of a single suspended device.

Table 1 shows preliminary data for a sensor fabricated with the suspended (etched) architecture as shown in FIG. 10 and a sensor fabricated with the planar (non-etched) architecture of FIG. 5, using the same coil geometry for both sensors. The preliminary data, at loads of 1960 N, 2940 N, and 3920 N, demonstrate that the resonance frequency shift using the suspended architecture is increased by 59%, 71%, and 45%, respectively, as compared to the unetched (planar) sensors. In addition, the signal quality factor is increased by almost 9% by employing the suspended architecture.

TABLE 1

|  | Load (N) | | | |
| --- | --- | --- | --- | --- |
|  | 1960 | 2940 | 3920 | Q-factor |
| Planar | 290 MHz | 380 MHz | 430 MHz | 93.81 |
| Suspended | 460 MHz | 650 MHz | 780 MHz | 102.06 |

Figure 12:
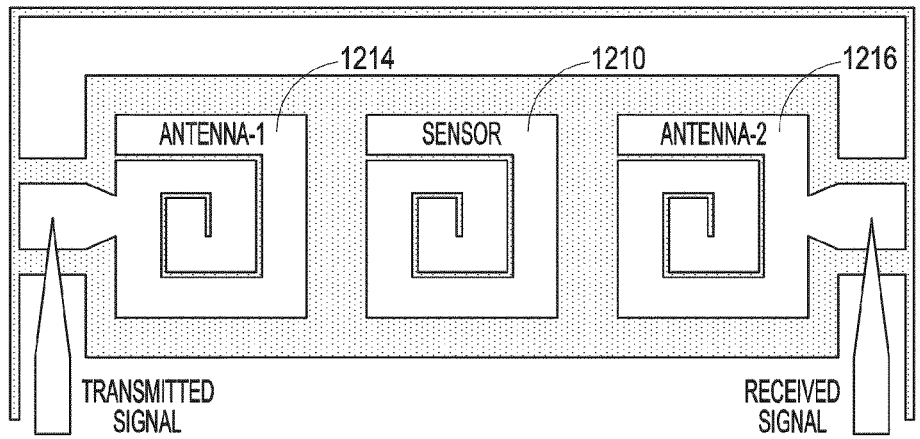
FIG. 12 shows an embodiment of a structure having a triplet configuration.

FIG. 12 shows an embodiment of a sensor structure having a triplet configuration. The triplet configuration can be arranged with triple rectangular coils, as three sensors arranged side-by-side. The sensors on the outside can act as a transmitter antenna 1214 and a receiver antenna 1216 for the middle sensor 1210. The individual coils in the triplet configuration can be constructed similar or identical to any of the coils discussed herein.

Figure 13:
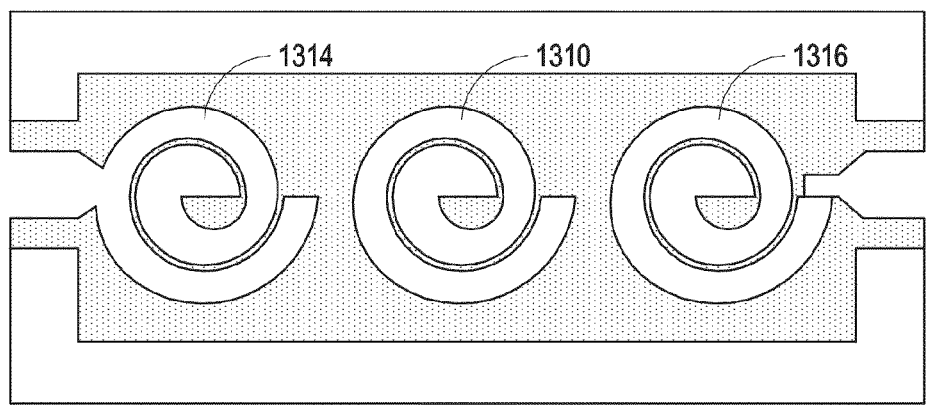
FIG. 13 shows an embodiment of a structure having a triplet configuration including a circular spiral coil.

FIG. 13 shows another embodiment of a structure having a triplet configuration. The structure includes three circular spiral coils 1310, 1314, and 1316. Circular spiral coils 1314 and 1316 can act as transmitters and receivers for middle sensor 1310. Alternatively, circular spiral coils 1310, 1314, and 1316 each operate as sensor resonators.

Figure 14:
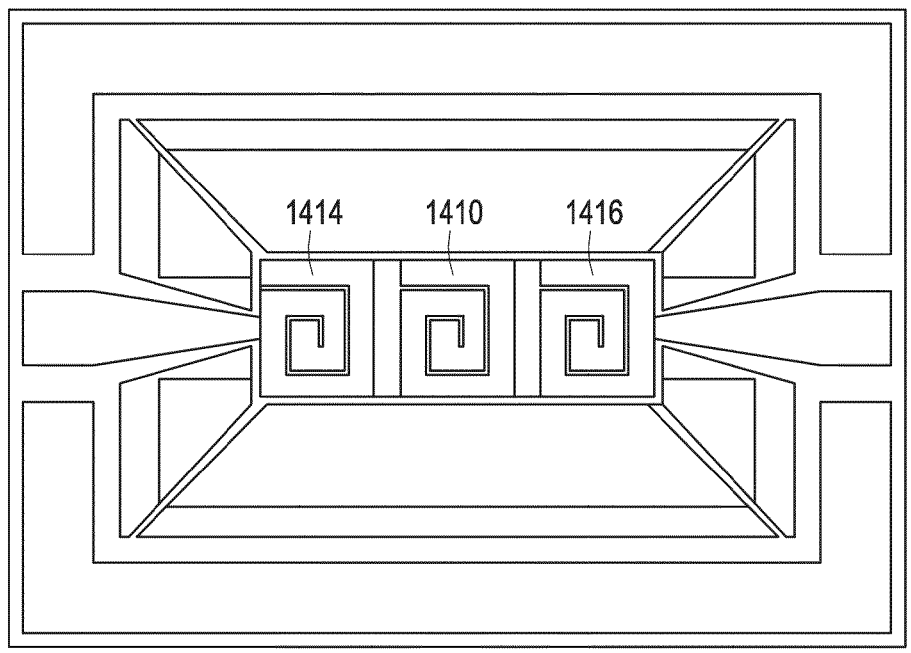
FIG. 14 shows an embodiment of a structure having a triplet configuration including a suspended coil resonator.

FIG. 14 shows another embodiment of a structure having a triplet configuration. The structure includes three suspended rectangular coils 1410, 1414, and 1416. Spiral coils 1414 and 1416 can act as transmitters and receivers for middle sensor 1410. Alternatively, spiral coils 1410, 1414, and 1416 each operate as sensor resonators.

Figure 15:
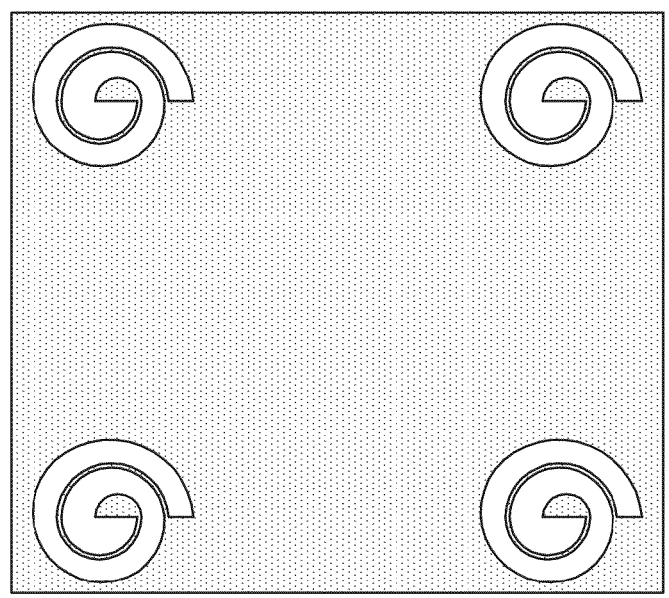
FIGS. 15-17 show various arrays of resonators on a chip.
Figure 16:
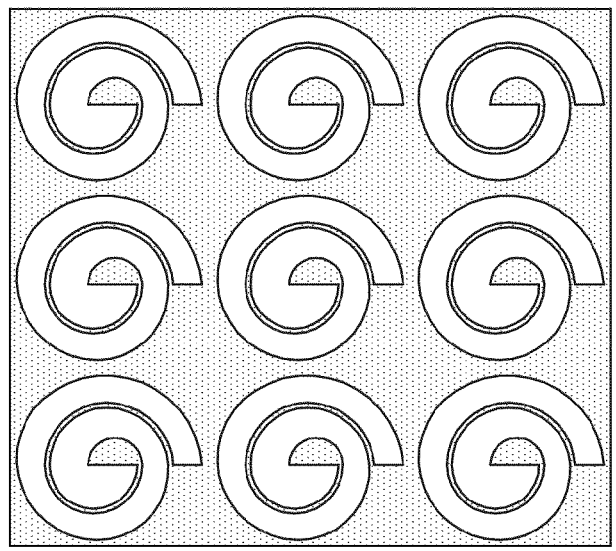
Figure 17:
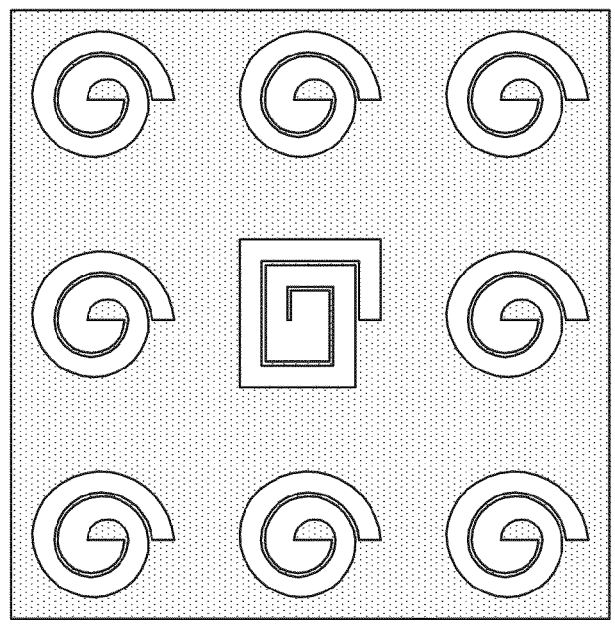

FIGS. 15-17 show various arrays of resonators on a chip. FIG. 15 shows four circular spiral coil resonators spaced relatively far apart. FIG. 16 shows an array with a number of circular spiral coil resonators. With increasing number of resonators in an array structure, the spacing between resonators decreases for a fixed size substrate. FIG. 17 shows an array with a number of circular spiral coil resonators and a rectangular coil resonator. Hybrid resonator arrays as shown in FIG. 17 are not limited to one rectangular coil resonator with a plurality of circular spiral coil resonators. A sensor can include a number of different type resonators, where the number for each individual type can vary.

Figure 18:
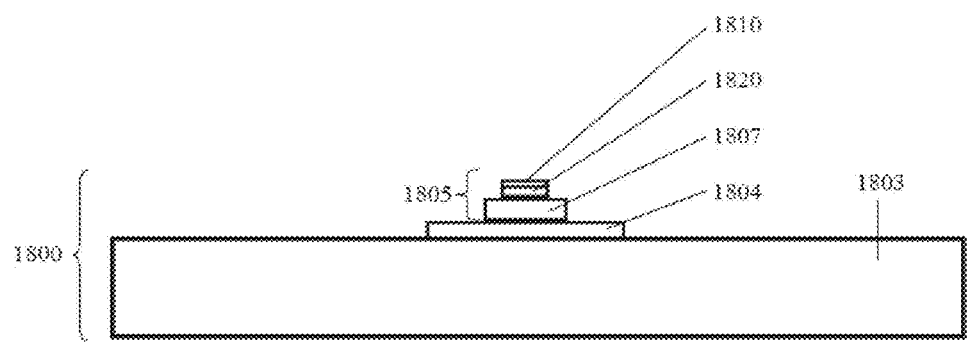
FIG. 18 shows an embodiment of an apparatus that is implantable into a biological subject.

FIG. 18 shows an embodiment of an apparatus 1800 that is implantable into a biological subject. The apparatus 1800 includes an orthopaedic hardware device 1803 and a sensor device 1805. The sensor device 1805 includes a substrate 1807, a dielectric material 1820 disposed over the substrate 1807, and a conductive coil 1810 disposed on the dielectric material 1820. The substrate 1807 can be disposed on the hardware device 1803. The dielectric material 1820 and the conductive coil 1810 are configured as a resonator. The substrate 1807 also can be arranged with the dielectric material 1820 and the conductive coil 1810 as a resonator. A solid biocompatible dielectric material can be used for the dielectric material 1820. The substrate 1807, the dielectric material 1820, and the conductive coil 1810 are configured or structured as a biocompatible, inductively powered sensor 1805. The hardware device 1803 and the sensor device 1805 can be implanted in a biological subject, such as a person or animal, to monitor the condition of the subject. When the hardware device is applied for healing of a bone fracture in the subject, changes in the strain of the hardware device, as detected by the sensor device 1805, can be used to determine changes in the healing of the bone fracture of the subject.

The sensor device 1805 can be attached to the hardware device using an epoxy 1804 for example. Solid biocompatible materials for the dielectric material 1820 can include, but are not limited to, silicon nitride. Solid biocompatible materials for the conductive coil 1810 can include, but are not limited to, gold. In addition to biocompatible properties, selection of materials for the sensor device 1805 can be based on capacitive and inductor properties. The sensor device 1805 can be similar to or identical to various embodiments of sensors described herein. For the sensor device 1805 constructed in the form of a tape-based flexible sensor, an external epoxy 1804 need not be used, because the tape can have its own epoxy or other attachment material or other ways of attachment.

Figure 19:
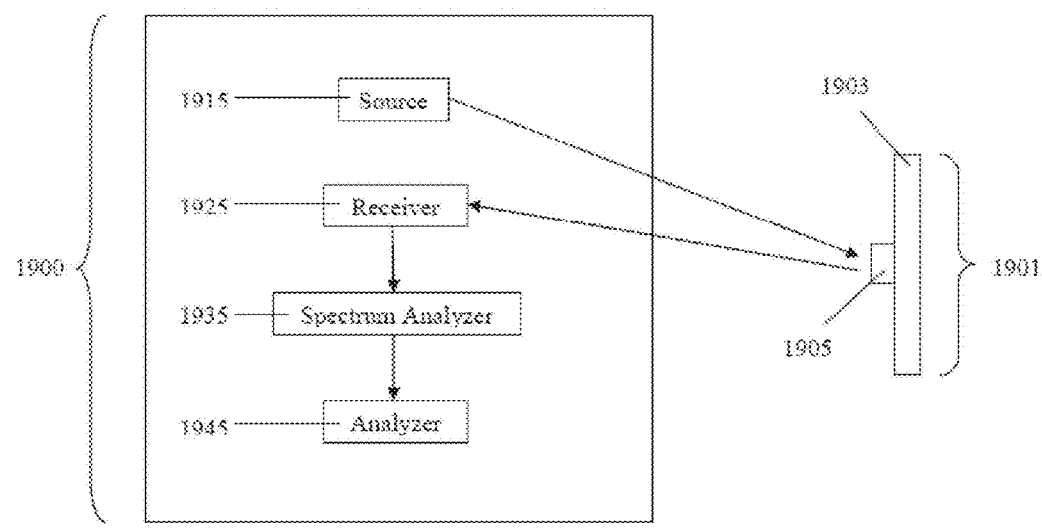
FIG. 19 illustrates an embodiment of a monitoring system for determining changes in hardware strain.

FIG. 19 illustrates an embodiment of a monitoring system 1900 for determining changes in hardware strain. Monitoring system 1900 includes a source 1915 operable to generate an electromagnetic field, a receiver 1925, a spectrum analyzer 1935, and an analyzer 1945. Source 1915 can generate an electromagnetic field to power a sensor 1905 with sensor 1905 attached to or integral with hardware 1903 implanted in a biological subject 1901. A sensor 1905 powered by the electromagnetic field is a biocompatible, inductively powered device that is used as a strain gauge for monitoring system 1900. Sensor 1905 can be similar to the sensors described with respect to various embodiments of sensors described herein.

Receiver 1925 is operable to receive signals from sensor 1905 generated in response to sensor 1905 being excited by electromagnetic fields at different times. Spectrum analyzer 1935 is operable to determine resonant frequencies of sensor 1905 from the received signals. Analyzer 1945 is operable to determine a temporal change in strain of the hardware, based on a shift in resonant frequency of sensor 1905 over time. The determination of the changes in hardware strain can be conducted based on a strain-frequency calibration of the hardware. Data from a strain-frequency calibration, performed prior to implantation, can be stored in memory accessible by analyzer 1945. Based on temporal changes in strain of the hardware, analyzer 1945 is operable to determine changes in the biological subject.

Monitoring system 1900 can include a machine-readable medium that stores instructions, which, when executed by a processor of the monitoring system, cause the monitoring system to perform various operations. These operations include, but are not limited to, controlling the excitation of sensor 1905, directing the determination of the resonant frequency of sensor 1905, controlling the determination of a shift in resonant frequency of sensor 1905 based on wireless signals from sensor 1905, where the wireless signals are generated from sensor 1905 in response to electromagnetic probe signals/fields applied at different times, and controlling the determination of a temporal change in strain of the hardware, based on the shift in resonant frequency. The machine-readable medium can include instructions to generate data representing fracture healing of the biological subject, where the data is based on the temporal changes in strain of the hardware implanted in the biological subject relative to the fracture. The machine-readable medium can be of any form that stores data, including instructions. For example, the machine-readable can be a computer-readable medium. The machine-readable may be separable from monitoring system 1900. The machine-readable can be a stand-alone apparatus that can be used in different systems.

To design an appropriate inductively powered sensor circuit, a coil geometry for an inductor can be used and transmission line theory applied to model this structure as a resonator. For use of these resonators as strain gauges implantable into a person, the design can be directed to obtaining a high quality RF signal using bio-compatible materials with a maximum, relative to various design trade-offs, possible resonance frequency shift per unit strain. In designing such a resonator, a number of parameters are considered. Such factors include substrate effects, dielectric thickness, dielectric material, choice of metal, metal layer thickness, line width and spacing, number of circuit turns, and total chip area. This approach utilizes the film capacitance of the sensor as the LC (inductance-capacitance) tank circuit capacitance. In various embodiments, the main driver of the observed change in the resonance frequency of the sensor is the capacitance change, as opposed to targeting changes in inductance. Since the sensor has a substrate and metal layer with a relatively high Young's modulus (stiffness), the resonance frequency shift is mainly due to the change in the capacitor area, and thus, overall capacitance.

Figure 20:
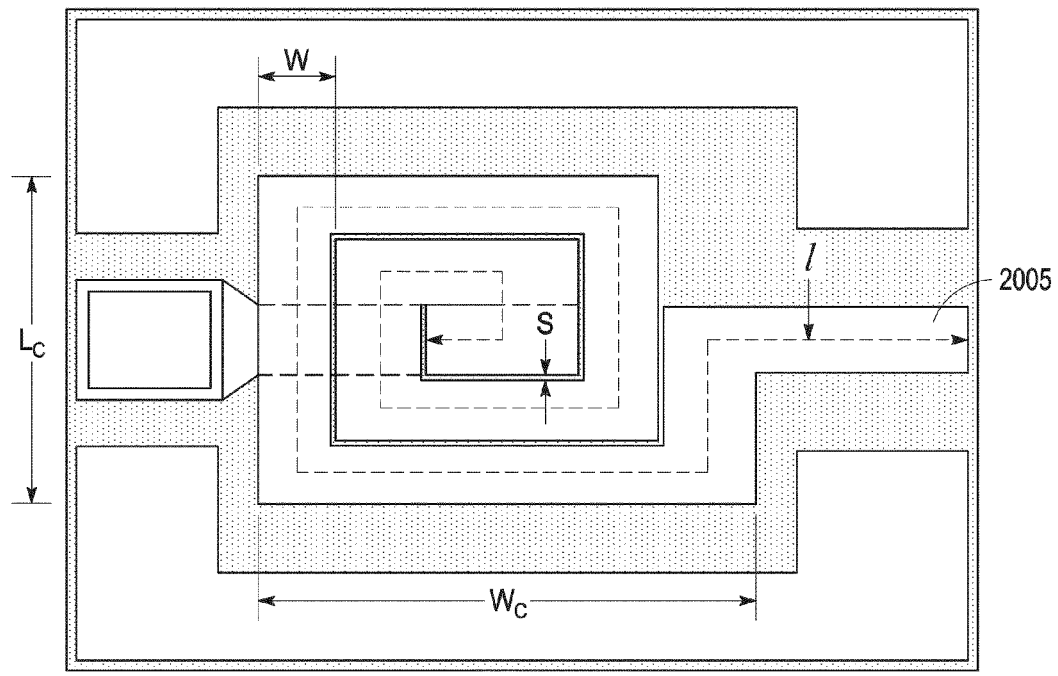
FIG. 20 shows an embodiment of an inductively, powered sensor.
Figure 21:
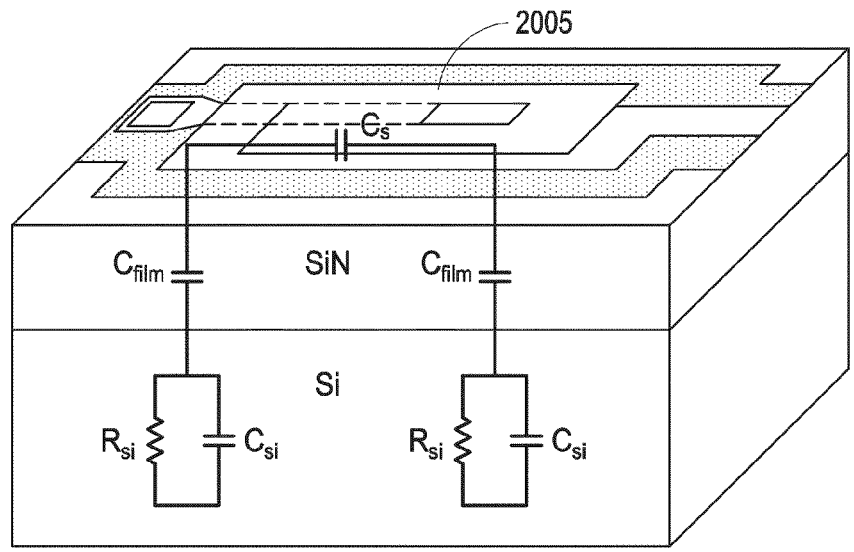
FIG. 21 shows a side view of the sensor of FIG. 20, including lumped-element representations of the physical model.
Figure 22:
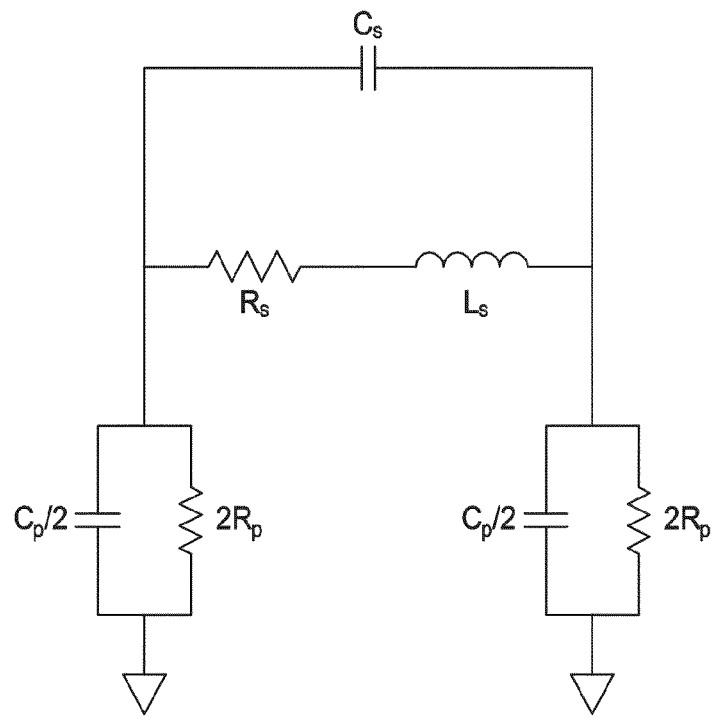
FIG. 22 shows an equivalent circuit of the resonator of the sensor of FIG. 20.

FIG. 20 shows an embodiment of an inductively powered sensor 2005. FIG. 21 shows a side view of sensor 2005 of FIG. 20 including lumped-element representations of the physical model. FIG. 22 shows an equivalent circuit of the resonator of sensor 2005. To model the device, the following design parameters are considered: the outer dimensional length ($L_c$) and width ($W_c$) of the coil; the total coil length (l); the total coil width (w); the line spacing (s); the number of turns (N); the coil thickness (t); and the thickness of the dielectric thin film between the substrate and the gold metal layer ($t_{film}$). The geometrical design parameters $L_c$, $W_c$, N, w, and s set the coil inner diameter. These device parameters are used to calculate the parameters for the lumped-element model illustrated in FIG. 22. Here, $L_S$ and $R_S$ correspond to the coil inductance and resistance, respectively. $C_{film}$ represents the capacitance between the substrate and the coil. $C_{Si}$ and $R_{Si}$ are the substrate capacitance and resistance, respectively. $C_s$ denotes the capacitance between the coil segments. The coil resistance ($R_S$) is a function of the skin depth, δ, which is the depth to which an incident electromagnetic wave can penetrate, where $R_s$ and δ are given in the following equations:

$$R_s = \frac{\rho l}{w\delta(1 - e^{\frac{t}{\delta}})}$$

where:

$$\delta = \sqrt{\frac{2\rho}{\omega\mu_0}}, \text{ and } \omega = 2\pi f$$

$C_{film}$ and $C_s$ are calculated using the classic parallel plate capacitor formulae:

$$C_{film} = \frac{\varepsilon_0 \varepsilon_r l w}{t_{film}}$$

$$C_s = \frac{\varepsilon_0 l t}{s}$$

where $\varepsilon_o$ and $\varepsilon_r$ are material permittivity coefficients.

$C_{si}$ and $R_{si}$, which represent substrate effects, are calculated using the following equations:

$$C_{Si} = 0.5 l w C_{sub}$$

$$R_{Si} = \frac{2}{l w G_{sub}}$$

where $C_{sub}=1.6\times10^{-10}$ F/cm² and $G_{sub}=0.4/\Omega\text{-cm}^2$ are empirically derived fitting parameters.

The capacitive and resistive circuit conversions, Cp and Rp, respectively, are obtained using the above calculated parameters:

$$R_p = \frac{1}{\omega^2 C_{film}^2 R_{Si}} + \frac{R_{Si}(C_{film} + C_{Si})^2}{C_{film}^2}$$

$$C_p = C_{film}\frac{1 + \omega^2(C_{film} + C_{Si})C_{Si}R_{Si}^2}{1 + \omega^2(C_{film} + C_{Si})^2 R_{Si}^2}$$

The preceding equations can be used to determine the theoretical expected capacitive shift due to changes in the sensors geometry, as a result of applied loading and associated deformation. With the sensor mounted on implantable hardware, the applied loading is transferred from the hardware. These formulae also provide a robust system for modeling design changes, such as varying the layer component thicknesses, and optimizing the capacitance of the system.

While the preceding provides a means of calculating the change in capacitance, the degree to which this shift is detectable is quantified as the circuit's quality factor (Q-factor). The total resonator Q-factor is given as follows:

$$Q\text{-factor} = \frac{f_0}{\Delta f}$$

where Δf is the half peak amplitude width and $f_0$ is the resonance frequency. Although the above equation is useful to extract the resonator quality factor from experimental characterization, it does provide information about which elements store or dissipate energy, which can be used to design a high-quality, on-chip resonator. Therefore, the definition of the Q-factor for the inductor is exploited instead of the entire LC tank circuit. For the inductor, only the energy stored in the magnetic field is of interest. Therefore, the maximum quality factor for the inductor ($Q_{ind}$) is attainable when the difference between the peak magnetic field and the peak electric field is at the maximum value. By this definition, which elements store and dissipate the energy can be ascertained and the design can be improved.

An alternate form for $Q_{ind}$ is given as:

$$Q_{ind} = \frac{R}{\omega L}\left[1 - \left(\frac{\omega}{\omega_o}\right)^2\right]$$

The above equation reveals that $Q_{ind}$ is zero at the structure's self-resonance frequency. This frequency for a classic LC circuit is given by:

$$f_0 = \frac{1}{2\pi\sqrt{LC}}$$

The resonator quality factor ($Q_{res}$) can be obtained by combining the inductor and the capacitor ($Q_c$) quality factors:

$$\frac{1}{Q_{res}} = \frac{1}{Q_{ind}} + \frac{1}{Q_c}$$

$Q_c$ is not extensively affected by structural design changes once the material system has been selected. $Q_{ind}$, on the other hand, depends on geometrical design as well as the material selection. Thus, by using the classic resonance definition and design techniques for better $Q_{ind}$, the resonator Q-factor for the small on-chip resonator can be designed towards maximization.

For optimizing $Q_{ind}$, one can start by simplifying the equivalent lumped-circuit model whose parameters were used to calculate $Q_{ind}$. Transforming the circuit to parallel the LC circuit and combining all the above equations, $Q_{ind}$ can be expressed as:

$$Q_{ind} = \left[\frac{\omega L_s}{R_s} \frac{2R_p}{2R_p + \left[\left(\frac{wL_s}{R_s}\right)^2 + 1\right]R_s}\right]\left[1 - \frac{R_s^2\left(\frac{C_p}{2} + C_s\right)}{L_s} - w^2 L_s\left(\frac{C_p}{2} + C_s\right)\right]$$

By parsing the above relationship for $Q_{ind}$, it can be shown that there are 2 portions of the equation that have different roles in determining the inductance quality factor contribution: (1) the substrate loss factor (SLF), which mainly affects the overall attainable (maximum) Q-factor; and (2) the self resonance factor (SRF), which mainly affects the resonance frequency:

$$SLF = \frac{2R_p}{2R_p + \left[\left(\frac{wL_s}{R_s}\right)^2 + 1\right]R_s}$$

$$SRF = 1 - \frac{R_s^2\left(\frac{C_p}{2} + C_s\right)}{L_s} - \omega^2 L_s\left(\frac{C_p}{2} + C_s\right)$$

Using these equations, the overall sensor geometry can be designed towards optimization of the quality factor ("Q-factor"), which a measure of the resonance peak sharpness defined as the peak magnitude divided by the half peak width, with minimum circuit spacing.

The materials for a bio-implantable sensor are selected under criteria that include biocompatibility. Although using gallium arsenide (GaAs) as a substrate material would enhance the Q-factor of the sensor, silicon (Si) can be used for its better biocompatibility characteristics. In various embodiments, a highly resistive Si substrate can be used. The selection of the dielectric layer affects the capacitance and the Q-factor. Silicon nitride ($Si_3N_4$) has a relatively high dielectric constant (as high as 8.0) and a low loss factor, and also it has been reported to be biocompatible. There are some dielectric materials that feature lower elastic (Young's) moduli than $Si_3N_4$, however, they have higher loss and lower dielectric constants, resulting in a low Q-factor and the change of resonance frequency has been calculated to be significantly lower than that of $Si_3N_4$. As a result, considering the trade-off between high Q-factor, small dimensions, and high shift of resonance frequency, $Si_3N_4$ can be used as the dielectric layer. Although aluminum (Al) and copper (Cu) are most frequently utilized as metallic components in MEMs devices, these materials have been largely recognized as being non-biocompatible. Instead of these metals, gold (Au) can be used as the metal layer for the coil.

Sensor design constraints such as a high Q-factor and small allowable dimension are taken into consideration when deciding on the material layer thickness and overall sensor fabrication. One approach is to design towards maximizing capacitance, which can be obtained from the tank circuit capacitance, as opposed to considering this element as a parasitic capacitance. The factors with respect to designing to capacitance include dielectric film thickness, metal layer dimensions, number of turns of the coil, and chip area/diameter. Based on modeling, a dielectric film thickness ($t_{film}$) of approximately 0.1 μm can be used. Other thicknesses can be used.

With respect to the effect of the substrate, minimizing substrate losses is important to achieve a considerable increase in $Q_{ind}$ and $Q_{max}$, as the substrate is the main lossy component in the system. With respect to a silicon substrate, for low loss, a high $R_{si}$ (a highly resistive substrate) is used. However, a completely nonconductive substrate would hinder the formation of a parallel-plate capacitor between the metal layer and substrate, which may not be appropriate for an on-chip resonator. In an embodiment, a substrate at 5-10 Ω·cm can be selected, which is sufficiently resistive to prevent excessive loss but still sufficiently conductive to serve as the second plate of a parallel-plate capacitor.

With respect to the effect of the dielectric thin film, the dielectric layer is also an important factor for a high-Q-factor design. To optimize the capacitor between the metal and the substrate, which serves as the C of the LC circuit, a dielectric layer with a high dielectric constant is appropriate. On the other hand, to minimize the loss, a low-loss dielectric is appropriate. $Si_3N_4$, with a dielectric constant of eight and a loss tangent of $5 \times 10^{-4}$, can be an appropriate selection as the dielectric film.

With respect to the effect of the film thickness, the thickness of the dielectric layer ($t_{film}$) is another effective parameter to design a high-Q-factor resonator. The selected dielectric-layer thickness may depend on the target resonance frequency for the resonator. With respect to the effect of the metal-layer parameters, the thickness of the metal layer is also significant to determine $Q_{ind}$. The thicker the metal is, the higher $Q_{ind}$ and $Q_{max}$ are. A metal thickness of 0.1 μm can be selected to limit use of special fabrication steps in a CMOS process. In spite of the thin layer, a high $Q_{ind}$ can be achieved by decreasing the substrate loss sufficiently. In that case, increasing the metal thickness would still affect the Q-factor but not as significantly as it would in a structure with a substrate resistance that is too low.

With respect to metal layer dimensions, to realize a high-performance sensor, the width of the metal layer can be an important design issue because an increase in the width produces an increase in the Q-factor and the resonance frequency, but this is associated with an inherent increase in the overall area (and dimension). In addition, the metal spacing affects the device performance. A lower spacing increases resonance frequency and leads to a more compact chip. However, an increased width and decreased spacing leads to parasitic effects which would decrease the overall Q-factor.

With respect to the effect of the number of turns, to increase $Q_{ind}$ while keeping the size small, the number of turns (N) can be decreased. This decreases the net inductance, pushing the self-resonance frequency higher. In various embodiments, the number of turns is set to two to produce a full coil. However, a coil with more or less turns can be used, which may depend on the architecture of the coil structure.

With respect to the effect of the area, the chip size can be influential to adjust the resonance frequency and $Q_{ind}$. Decreasing the total area leads to an improved Q-factor and a higher resonance frequency. Also, a smaller inner diameter increases the Q-factor and resonance frequency. However, decreasing the inner diameter to a point where it is less than the spacing causes additional parasitic effects.

With respect to the effect of the inner diameter, if all the other design parameters are fixed, the increase in inner diameter increases the area. This decreases the resonance frequency and, hence, $Q_{ind}$. Therefore, a smaller inner diameter enhances $Q_{ind}$ and the resonance frequency. However, the inner diameter can be selected to only decrease the inner diameter down to the thickness of the spacing s, since decreasing below this value causes the parasitic capacitance to dominate and degrade $Q_{ind}$.

The geometric factors can be used to determine the resistance and capacitance of a sensor for used as an implantable device operable as a wireless without an incorporated power supply. $R_p$, which is shown in FIG. 22, represents the combined resistance of the coil model of FIG. 21 and is an effective component to determine the substrate losses. With a high-resistivity silicon substrate, the value of $R_{Si}$ is high, which provides a high $R_p$. $C_p$ corresponds to the capacitive component of the sensor and has a significant effect on the self-resonance factor. Lower $C_p$ results in enhancements to the resonance frequency, which aids in determining changes in strain as discussed herein. Biocompatible materials other than silicon and silicon nitride can be used with their corresponding parameters used in the equations discussed above.

Various fabrication processes can be used to construct inductively, powered sensors to wirelessly report information for the transient load transfer profile between bone and implanted hardware. The fabrication process selected depends on the components for the chip-sized sensor. Variations in processes depend on such factors as coil design and whether the substrate includes a flexible tape or is structured without a tape. In various embodiments, the fabrication process is a multi-step procedure that uses conventional MEMs processes. The sensor can be processed in a clean room environment using microwave-compatible, photolithographic microfabrication techniques.

Figure 23:
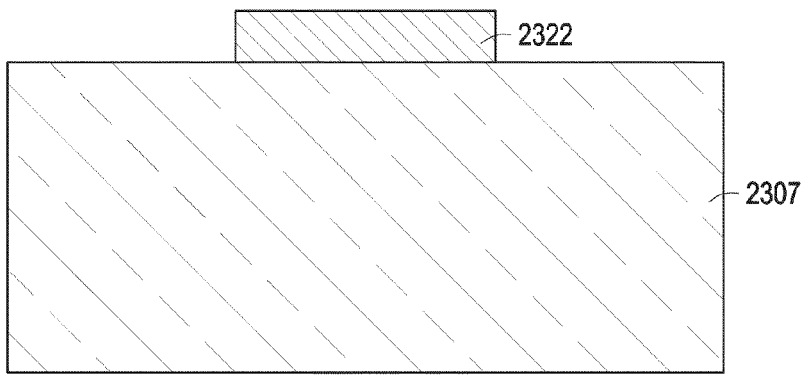
FIGS. 23-27 show an example embodiment of a fabrication process flow that can be used to manufacture a sensor device.
Figure 24:
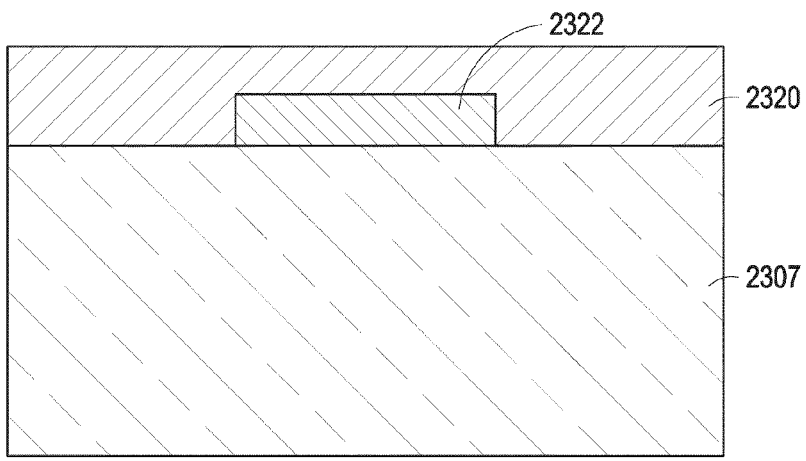
Figure 25:
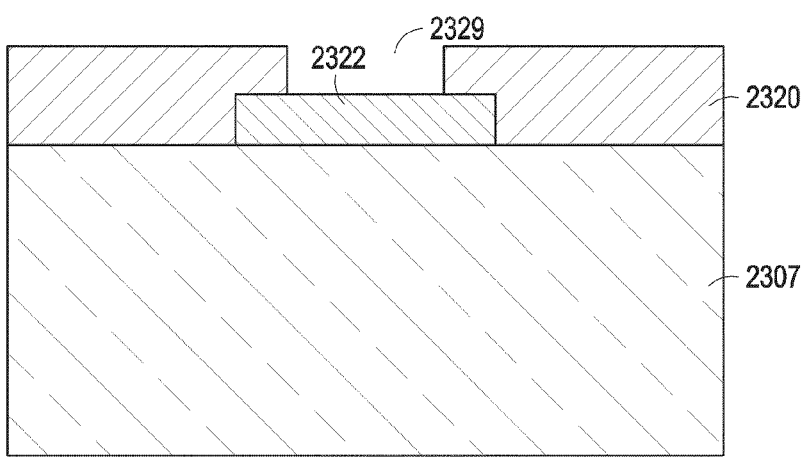
Figure 26:
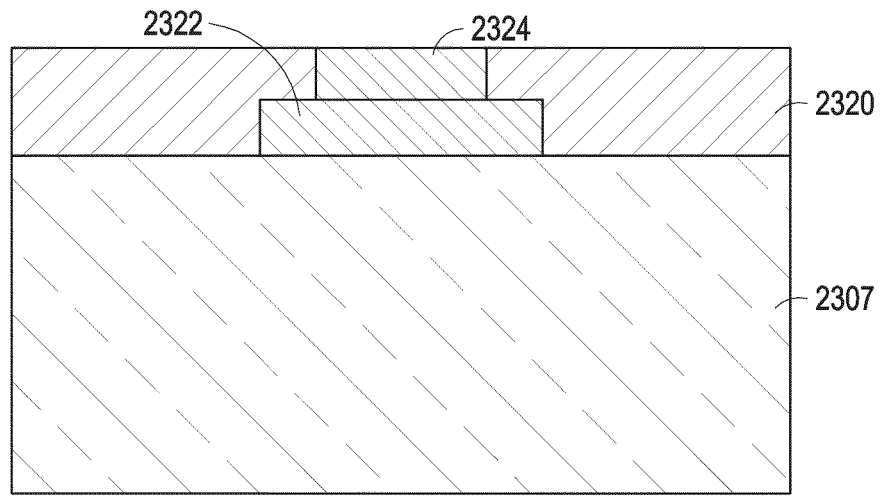
Figure 27:
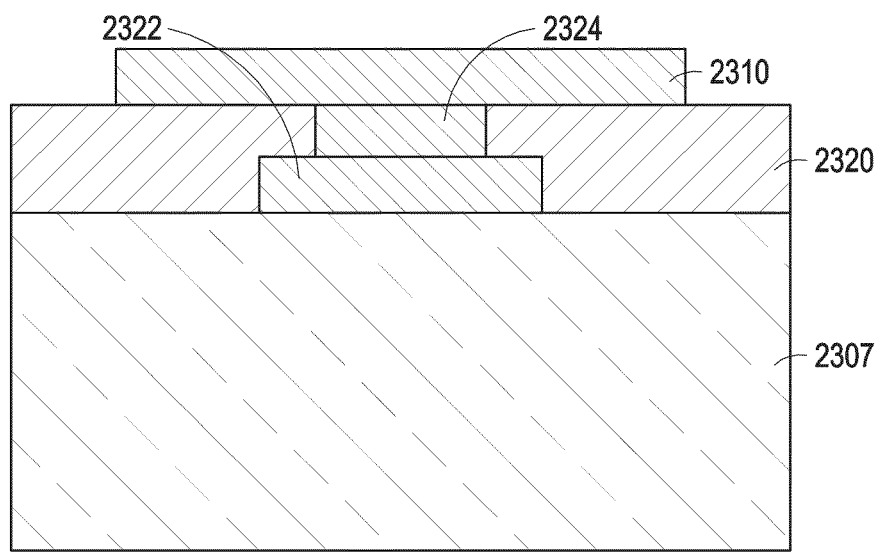

FIGS. 23-27 show an example embodiment of a fabrication process flow that can be use to manufacture a sensor device such as sensor 2005 of FIG. 20. With this sensor having a silicon substrate, a first step includes standard lithography and liftoff directly on a Si substrate 2307 to lay down the first gold (Au) metal layer 2322 as shown in FIG. 23. Plasma-enhanced chemical vapor deposition (PECVD) can be used to deposit a silicon nitride ($Si_3N_4$) thin film 2320 as shown in FIG. 24. Other deposition processes can be used to deposit $Si_3N_4$ thin film 2320. To pattern the $Si_3N_4$ film 2320, a second lithography is performed to open vertical interconnection areas 2329, such as using a wet etching process with hydrofluoric acid, as shown in FIG. 25. In a subsequent Au metallization, the interconnection layer 2324 is erected, as shown in FIG. 26. As shown in FIG. 27, a third lithography and Au metallization processes can be used to construct the top coil 2310 in order to obtain the sensor resonator.

Figure 28:
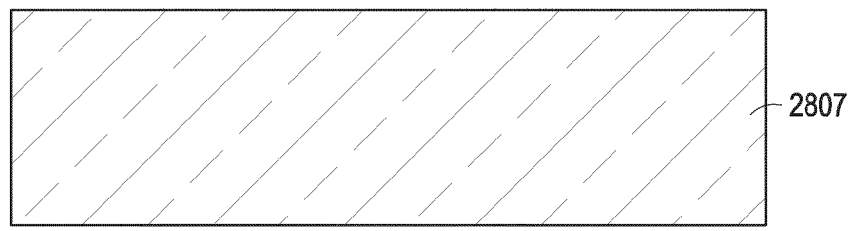
FIGS. 28-31 illustrate an embodiment for fabricating a tape-based flexible sensor.
Figure 29:
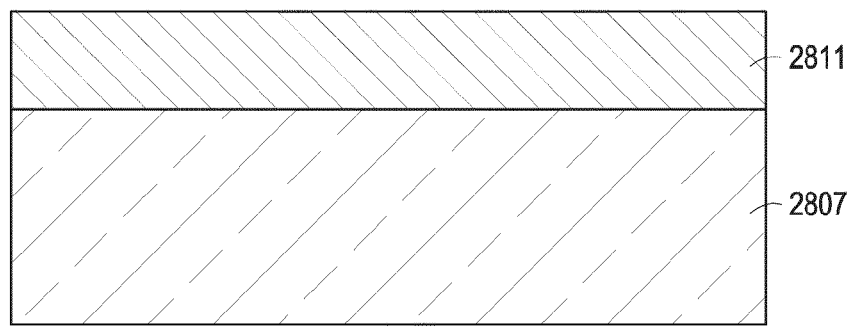
Figure 30:
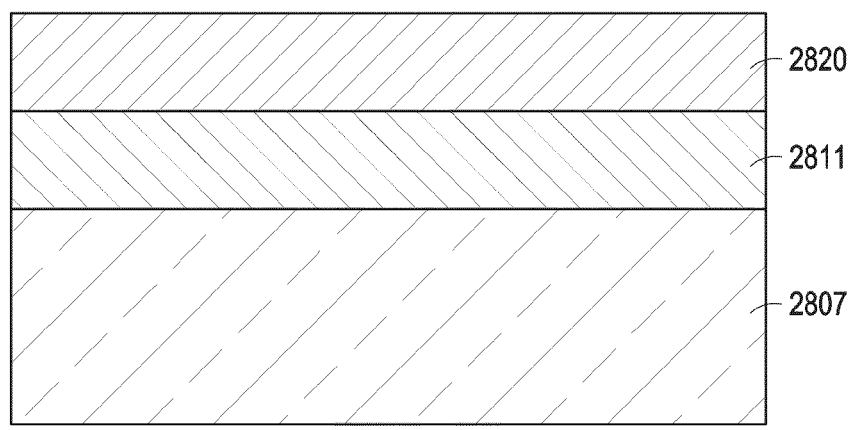
Figure 31:
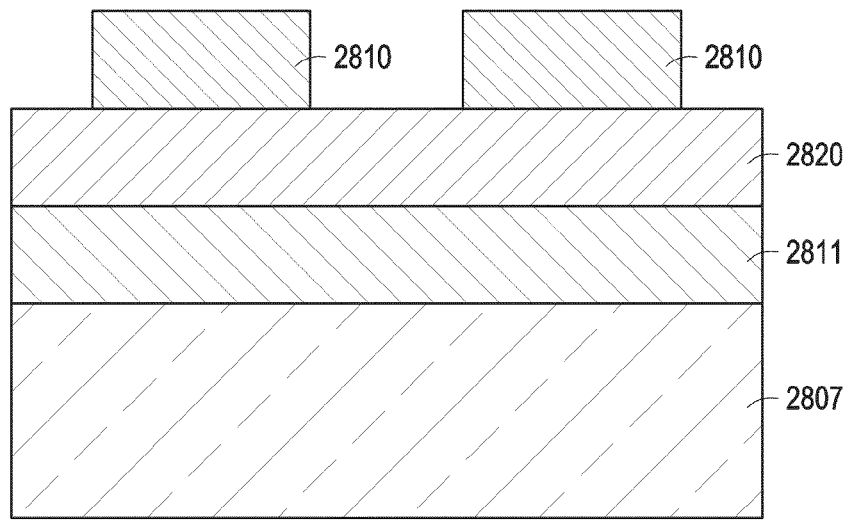

FIGS. 28-31 illustrate an embodiment for fabricating a tape-based flexible sensor. FIG. 28 shows a vacuum tape 2807 for use as a flexible tape substrate. FIG. 29 shows a thin gold layer 2811 deposited on flexible tape substrate 2807, where the deposition can use standard metallization techniques. Using plasma enhanced chemical vapor deposition (PECVD), an equally thin layer 2820 of $Si_3N_4$ can be deposited as the dielectric thin film, as shown in FIG. 30. Using standard lithography, metal evaporation, and lift-off techniques, a gold layer 2810 can be deposited to form the sensor fabrication, as shown in FIG. 31.

Vacuum tape 2807 can be used, since it can withstand the high temperatures encountered under PECVD. A difference of the fabrication procedure between the tape-based flexible sensor and the silicon-based sensor includes the deposition of the first gold layer 2811 onto the vacuum tape substrate 2807. The first gold layer 2811 increases the absorption of the sensor at the resonance frequency so that a large dip can be seen at the resonance frequency. However, with a silicon substrate, the silicon itself increases absorption so that the sensor can be formed without the extra Au layer.

Figure 32:
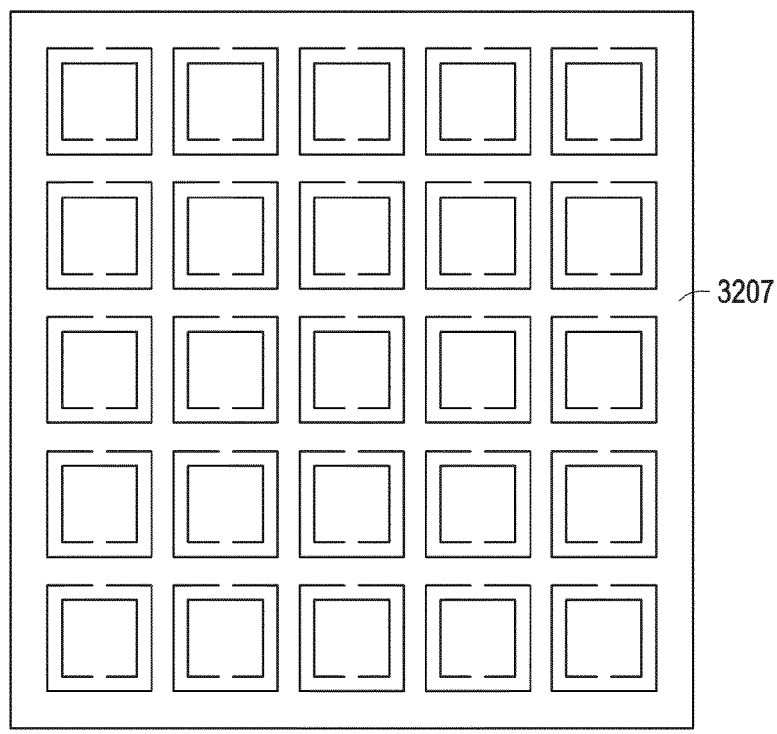
FIG. 32 shows a final fabricated structure on a flexible tape substrate.

Deposition of the first gold layer 2811 also provides for the parallel plate capacitor, which is the capacitor formed by between the first and final gold layers 2811, 2810 on opposite sides of thin layer 2820 of $Si_3N_4$ of the tape-based flexible sensor. However, for the silicon substrate-based sensor with a doped silicon substrate, a parallel plate capacitor is formed without an extra Au layer, because the doped silicon is conductive. The parallel plate capacitor is an important feature for the sensor, because when the load is applied, the parallel plate capacitor will change and as a result, the resonance frequency will change. FIG. 32 shows a final fabricated structure on a flexible tape substrate 3207. The final fabricated structure shown in FIG. 32 includes a metamaterial sensor. Other geometrical arrangements can be formed on flexible tape substrate 3207.

Figure 33:
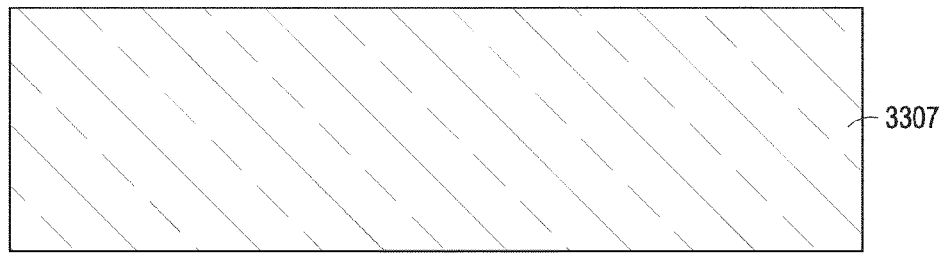
FIGS. 33-41 illustrate an embodiment of a method for forming a sensor in a suspended architecture.
Figure 34:
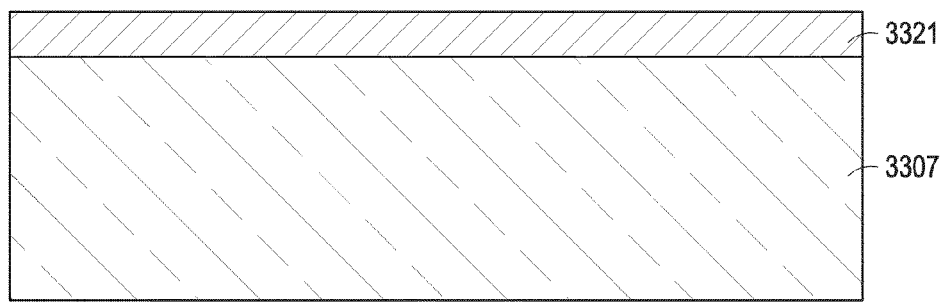

FIGS. 33-41 illustrate an embodiment of a method for forming a sensor in a suspended architecture. The process can be initiated with the selection of a substrate 3307, as shown in FIG. 33. A n-type 500 µm thick silicon substrate 3307 with a <100> orientation can be used. Other materials and/or conductivity types can be used for the substrate. A $Si_3N_4$ thin film 3321 can be deposited using a plasma-enhanced chemical vapor deposition system, as shown in FIG. 34. Other deposition processes and other dielectric materials can be used. $Si_3N_4$ thin film 3321 can be 0.1 µm thick. Other thicknesses can be used.

Figure 35:
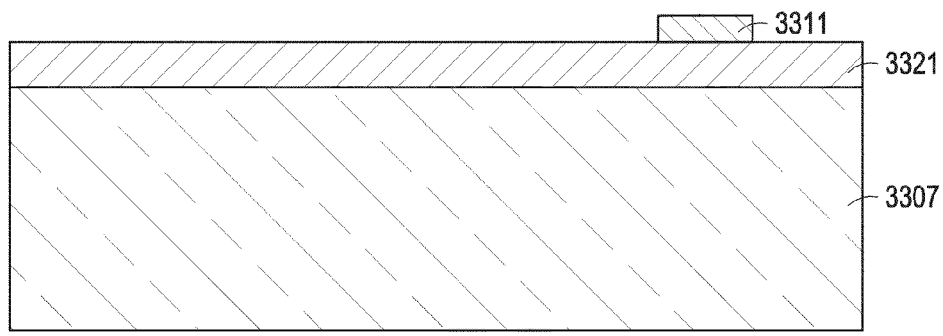
Figure 36:
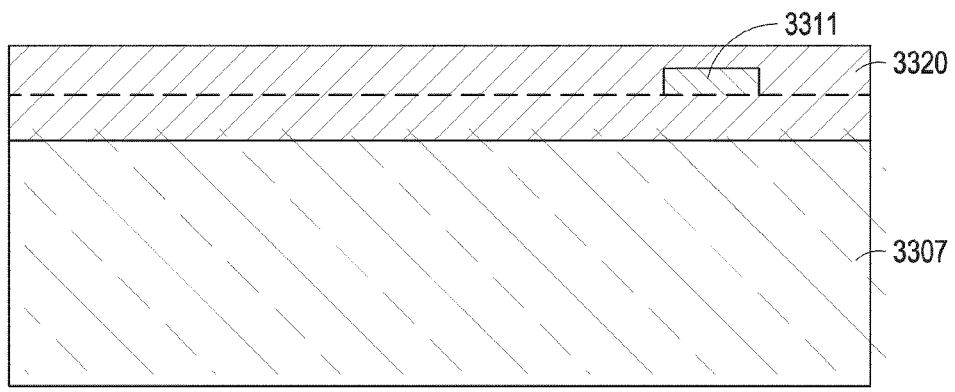

FIG. 35 shows a first metal layer 3311 laid down on $Si_3N_4$ thin film 3321. First metal layer 3311, formed as a contact layer, can be made of Au with a thickness of 0.1 µm. Other thicknesses can be used and/or other conductive materials can be implemented. FIG. 36 shows a subsequently deposited dielectric film 3320. The dielectric film 3320 can be a 0.1 µm thick $Si_3N_4$ thin film.

Figure 37:
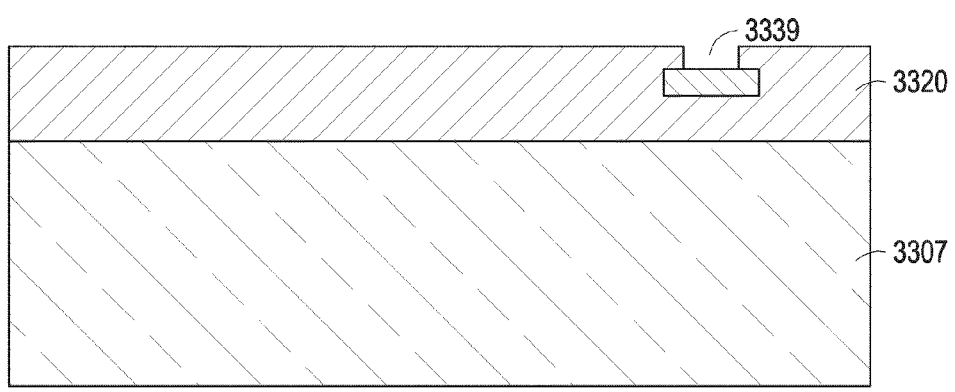
Figure 38:
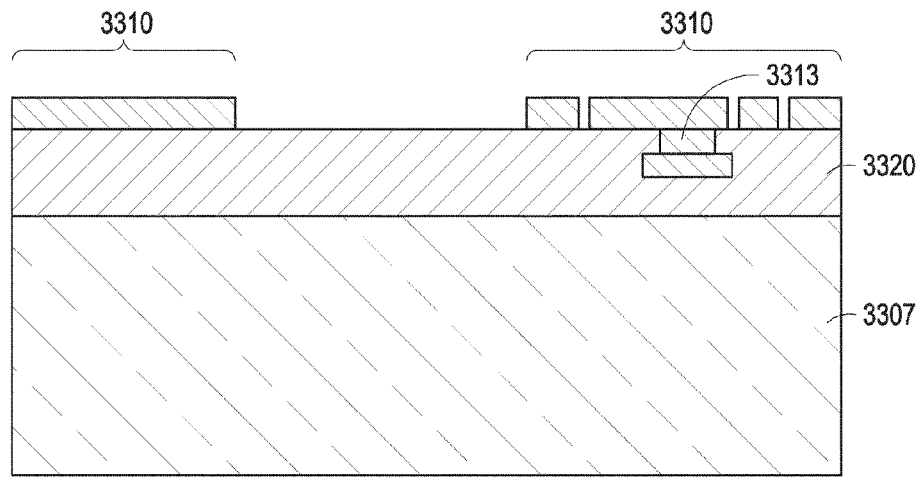
Figure 39:
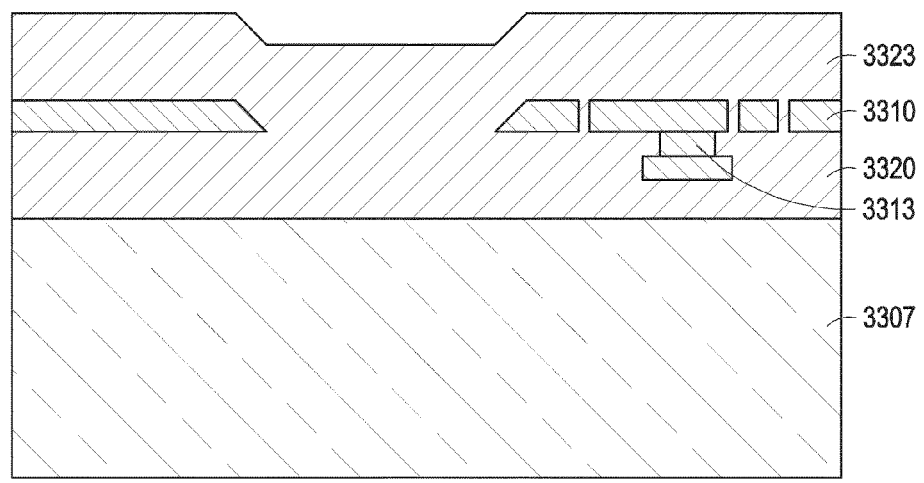
Figure 40:
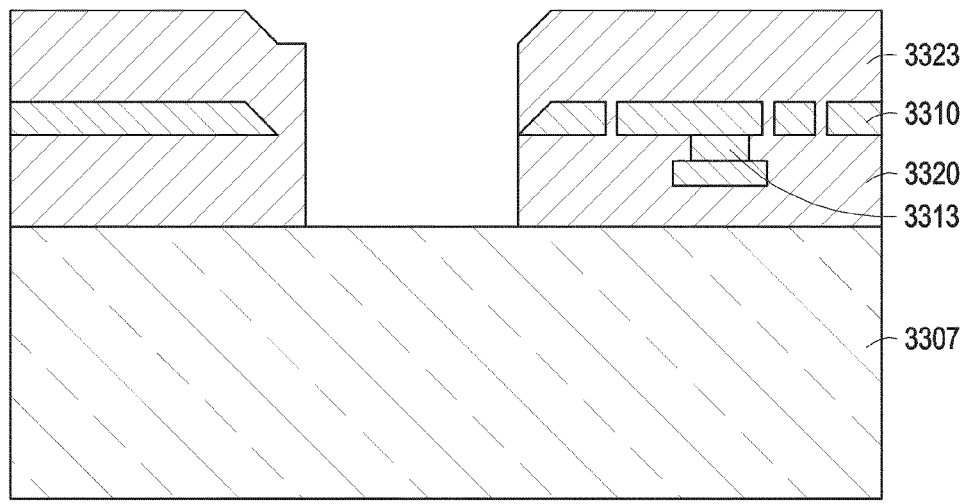
Figure 41:
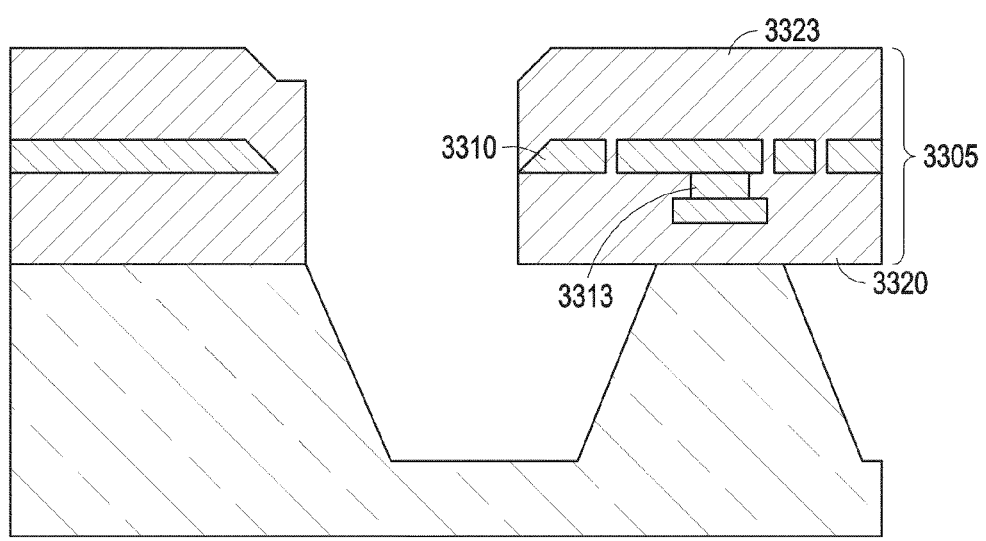

FIG. 37 shows film 3320 after patterning and forming vertical interconnection areas 3339, which can be opened for example using a wet etching process with HF. FIG. 38 shows the structure after performing a gold metallization to form the interconnects 3313 and top coil construction 3310. A 0.8 µm thick $Si_3N_4$ film 3323 can be deposited, as shown in FIG. 39. Silicon nitride film 3323 can be patterned and etched by HF, as shown in FIG. 40. FIG. 41 shows the structure after etching the silicon, such as using potassium hydroxide (KOH), to form the suspended sensor 3305.

Figure 42:
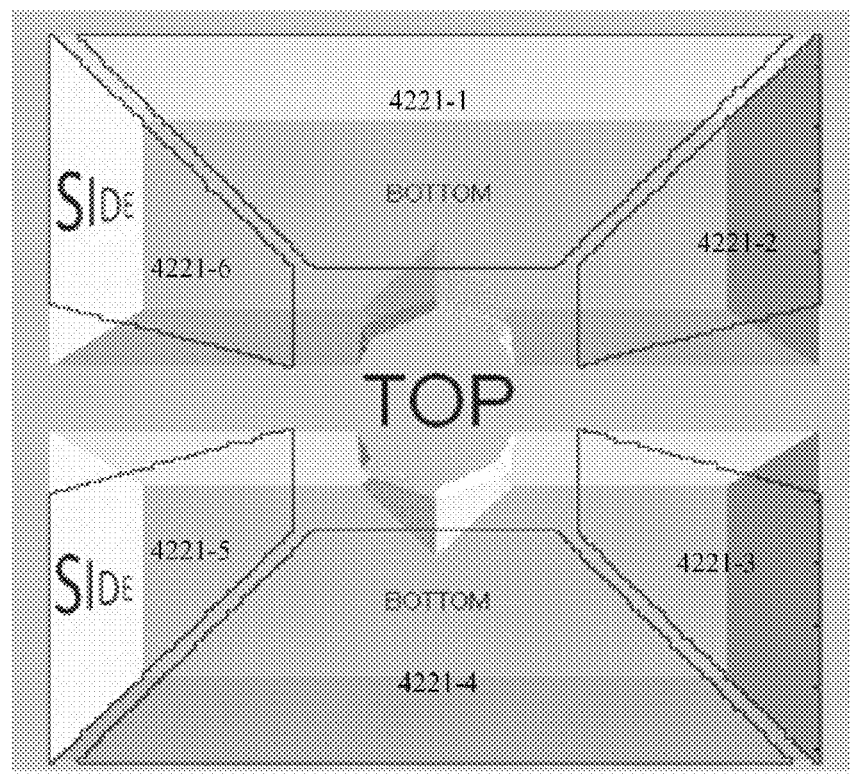
FIG. 42 shows a simulation of a suspended resonator.

The $Si_3N_4$ thin film is initially formed to protect the contact metal layer, while silicon is being etched. Since KOH also etches the metal layer, the first and third $Si_3N_4$ layers are used as etch-stop layers. The second $Si_3N_4$ layer with the first $Si_3N_4$ layer acts as the dielectric layer for sensor resonator 3305. Using a KOH solution with a concentration of 30 percent gives an etch rate of 1.1 µm/min, as expected from chemical kinetics simulations of silicon etching. After 70 minutes, a depth of 77 µm is etched. FIG. 42 shows a simulation of a suspended resonator. Trapezoids 4221-1, 4221-2, 4221-3, 4221-4, 4221-5, and 4221-6 represent areas in which $Si_3N_4$ is absent. KOH solution etches the silicon through these regions. An associated SEM image of a single suspended device is shown in FIG. 11.

Figure 43:
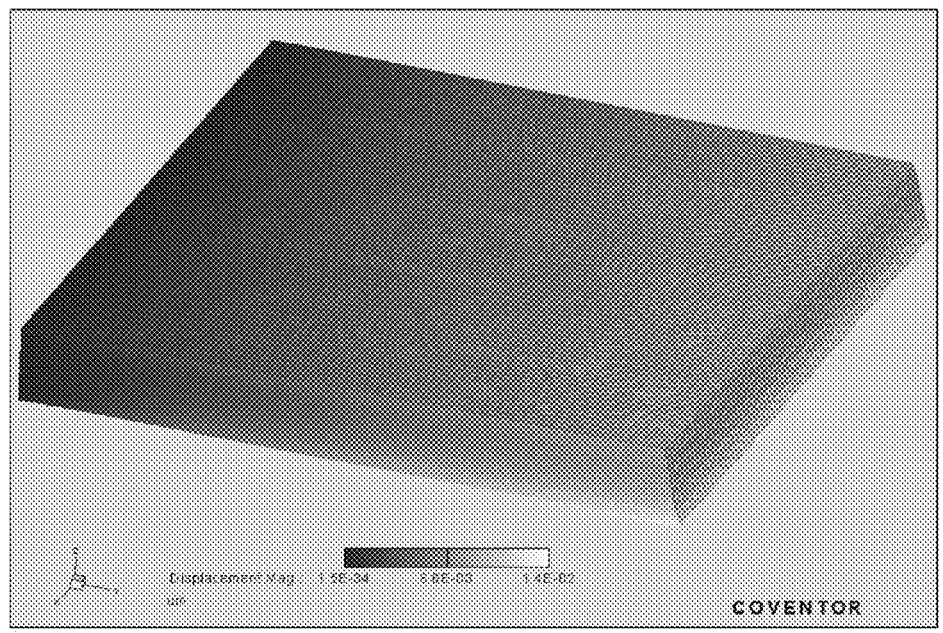
FIG. 43 shows an example of a model prediction of a deformed sensor device under application of a bending load, in terms of a resulting displacement field.

Analytical and numerical models can be used to simulate the performance of a sensor as a function of the mechanical perturbations induced on the device. The modeling effort includes use of coupled electromechanical analysis involving two interdependent components. A first step involves a mechanical analysis that computes the device's strain profile resulting from applied loading exerted on the sensor. The second is an electrical analysis that computes the shift in the sensor resonant frequency given the changes in its physical dimensions. Taking the relevant geometric factors into account in a simulation, such as with a finite element software package, the strain induced in the device, when different bending loads are applied, can be predicted. FIG. 43 shows an example of a model prediction of the deformed device under application of a bending load, in terms of a resulting displacement field. From the simulation, it can be observed that the area of the dielectric film changes, modifying the value of $C_{film}$. Based upon these dimensional changes, the inductance of a spiral coil ($L_s$) can be calculated, using a form of the equations above.

different sensor geometries. $L_C$ and $W_C$ represent the total length and total width of the device, respectively; N is the number of turns; w is the width of each coil; s is the spacing between coils; $t_{film}$ and $t_{metal}$ represent the thickness of the dielectric film and the thickness of the metal, respectively; and theoretical $L_s$ and numerical $L_s$ represent the inductance values from analytical and simulation models, respectively.

TABLE 2

| | $L_c$ (μm) | $W_c$ (μm) | N | w (μm) | s (μm) | $t_{film}$ (μm) | $t_{metal}$ (μm) | Theoretical $L_S$ (nH) | Numerical $L_S$ (nH) |
|---|---|---|---|---|---|---|---|---|---|
| Sensor-1 | 340 | 340 | 2 | 60 | 10 | 0.1 | 0.1 | 2.854 | 2.842 |
| Sensor-2 | 270 | 270 | 2 | 50 | 5 | 0.1 | 0.1 | 2.260 | 2.244 |

Figure 44:
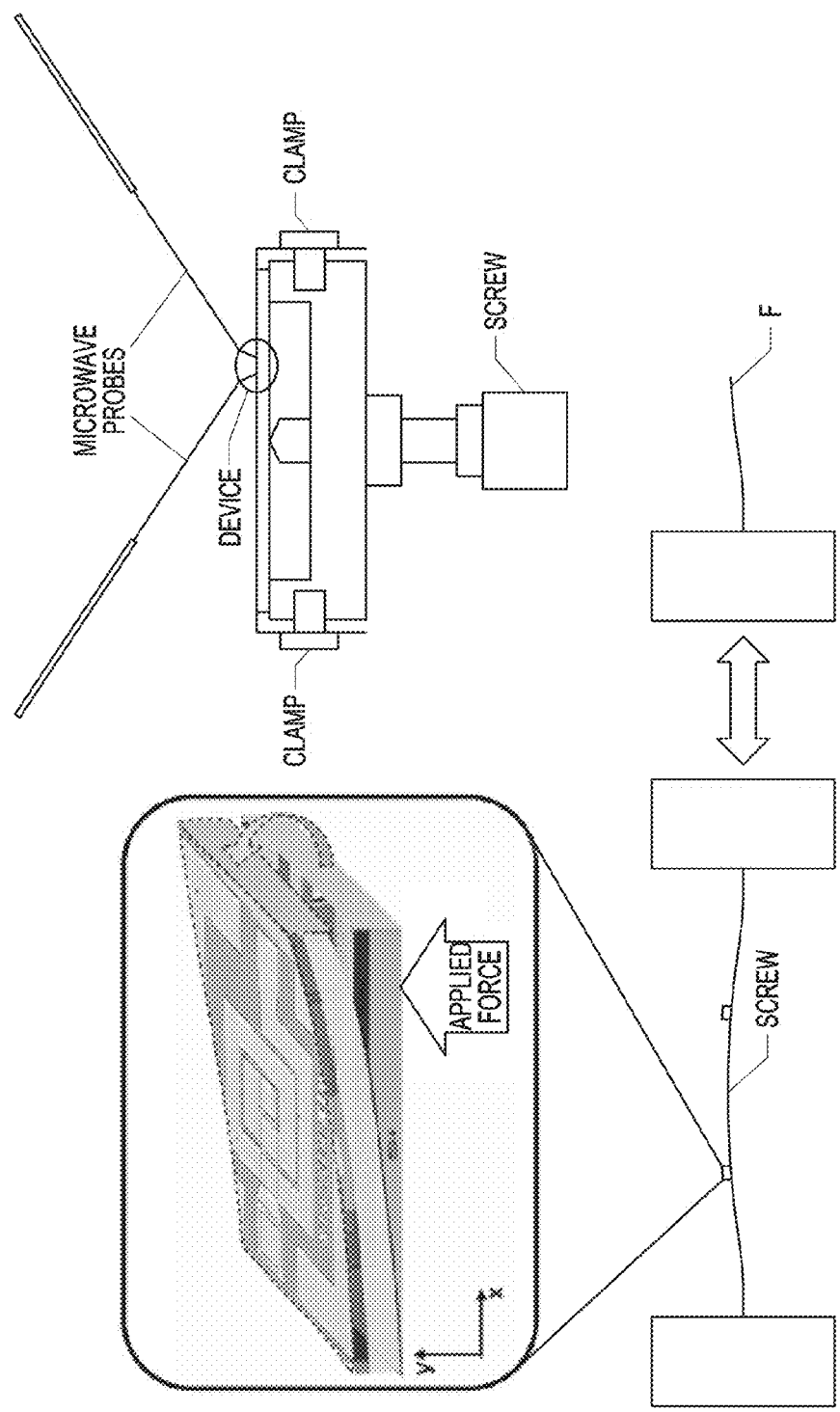
FIG. 44 shows an example of the application of loads in tension in a controlled manner.

Sensors attached to hardware can be tested using a experimental setup that includes mechanical and electromagnetic components. The mechanical apparatus enables the application of loads in tension in a controlled manner as shown in FIG. 44. Such application provides for conducting a series of physical experiments to investigate the resonance frequency shift response due to applied loads for different device geometries. The experimental characterization consists of applying a point load with an ultra-fine adjustable screw positioned below the kinematically-constrained silicon substrate to control and modify the load in a controllable manner. The $S_{21}$ parameter can be measured using a spectrum analyzer in conjunction with the microwave probes, before and after application of the load. The $S_{21}$ parameter is a measure of the RF signal efficiency and is calculated as the power density of the transmitted wave (essentially the output) per incident power (input).

Cast polyamide sticks can be used for testing, on to which the sensor is fixed using hard epoxy. Implantable sticks, having two holes, are secured in the set up by using fixation screws. Load is applied using the piston of the setup which pulls the secured stick. The applied load is tracked by the load cell as also shown in FIG. 44. Using this apparatus, loads can be applied up to 300 kgf. Other testing apparatus, which can apply higher loads, can be used.

For RF characterization, the antennas in FIG. 44 are made of coaxial probes with the same ground to decrease the noise in the characterization. Baluns can also be used, which use can decrease the general noise, caused by vibrations in the room, to a negligible level. In the set-up of FIG. 44, the length of these probes can be set to 2.5 cm. Because the sensor is so small in size in comparison to the operating wavelength, it is rather difficult to use standard antennas with sizes comparable to the sensor to measure its transmission spectra. In the set-up of FIG. 44, these probe antennas are placed 0.5 cm away from the sensor. In this configuration, the best signal may be obtained when the probes are parallel to the sensor. In various arrangements, these distance parameters are kept fixed throughout the calibration process and characterization process. For calibration purposes, the transmission of the stick, which is the hardware to which the sensor is attached, is measured first with no sensor chip attached on to the stick. Subsequently the same measurement is repeated with the sensor attached to the stick under no load and then also varying the external load applied with the mechanical apparatus. Calibrated with respect to the case of no sensor, the relative transmission spectra are obtained as a function of the applied load.

Figure 45:
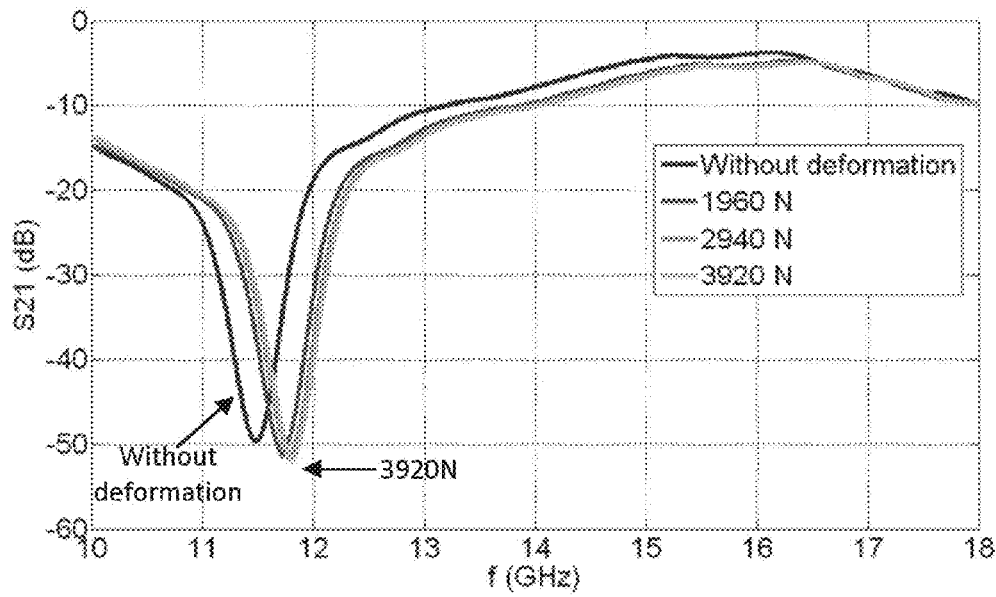
FIGS. 45-48 show the differences between the sensor responses of two sensors without any deformation (no load) and under different applied loads.
Figure 46:
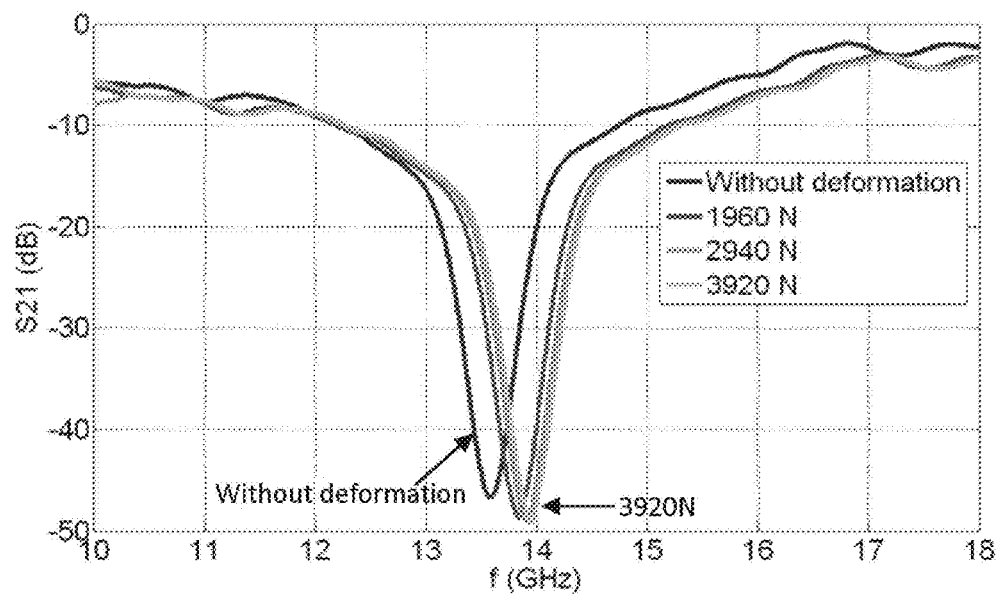
Figure 47:
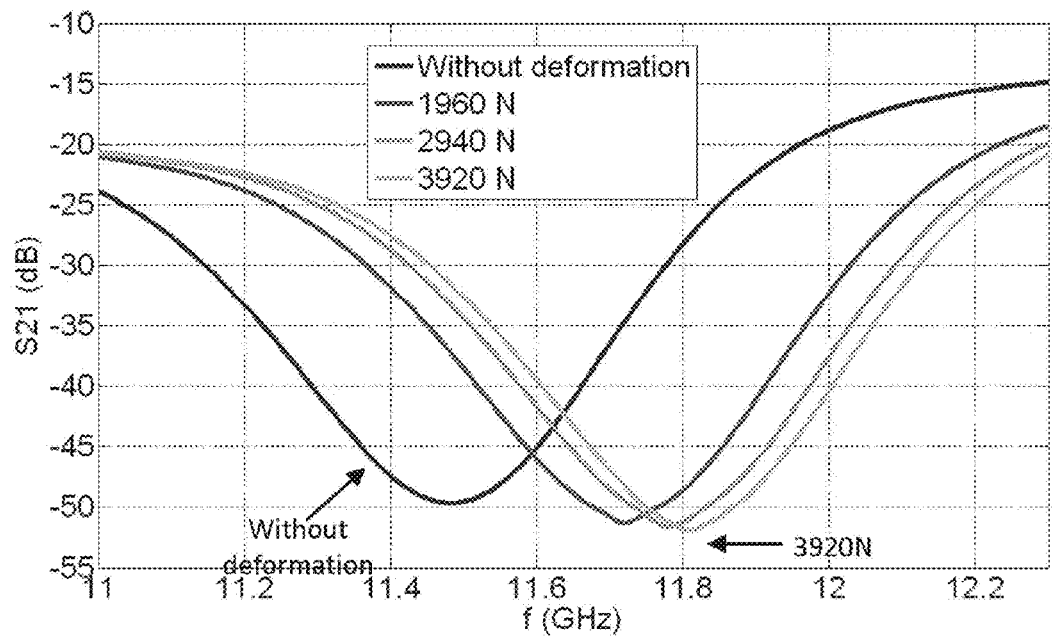
Figure 48:
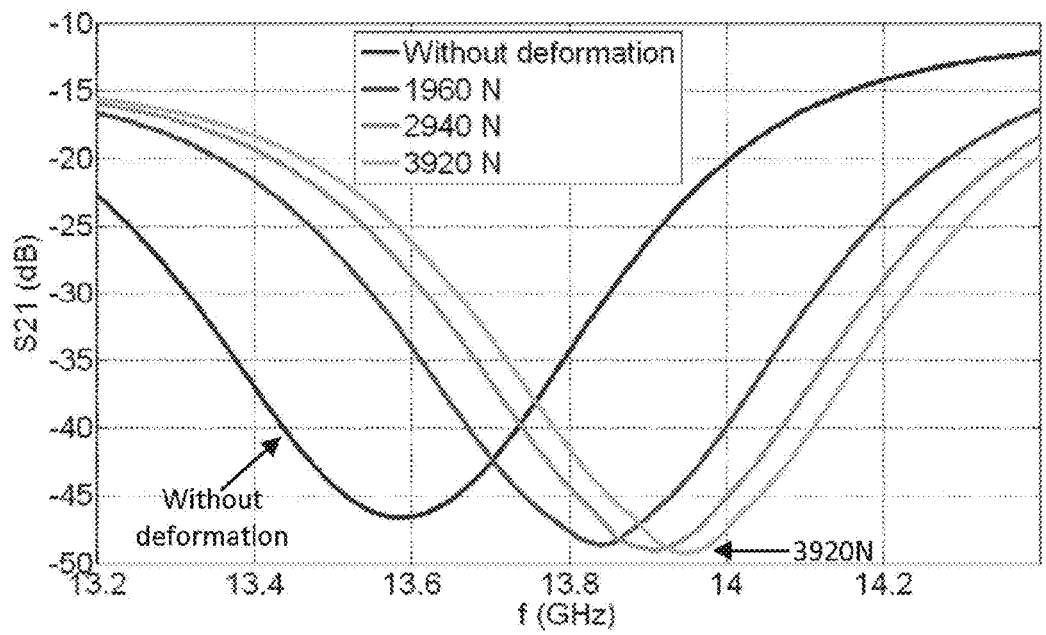

In an experiment, two sensors, sensor-1 and sensor-2, having different geometries, were fabricated and characterized. Table 2 shows the values of the parameters for these two FIGS. 45-48 show the differences between the sensor responses of sensor-1 and sensor-2 without any deformation (no load) and under different applied loads. As illustrated in FIGS. 45 and 47 (representing an enlarged view of FIG. 45 at the resonant frequency region), for sensor-1, the resonance frequency was measured to be 11.48 GHz with an associated Q-factor of 59.98 prior to load application. Under an applied load of 1960 N, the resonance frequency shifted by 240 MHz. With the same sensor, application of 2940 N and 3920 N resulted in resonance frequency shifts of 300 MHz and 330 MHz, respectively, relative to the unloaded configuration. Concomitant with the increase in resonant frequency shift with applied load, the Q-factor of the sensor also increased as evidenced by a measured Q-factor of 76.00 at a 3920 N applied load. These findings were similarly demonstrated with Sensor-2 as illustrated in FIGS. 46 and 48 (representing an enlarged view of FIG. 46 at the resonance frequency region. In short, the resonance frequency increases (i.e., shifts toward the right as shown in FIGS. 45-48) as the applied load increases.

Figure 49:
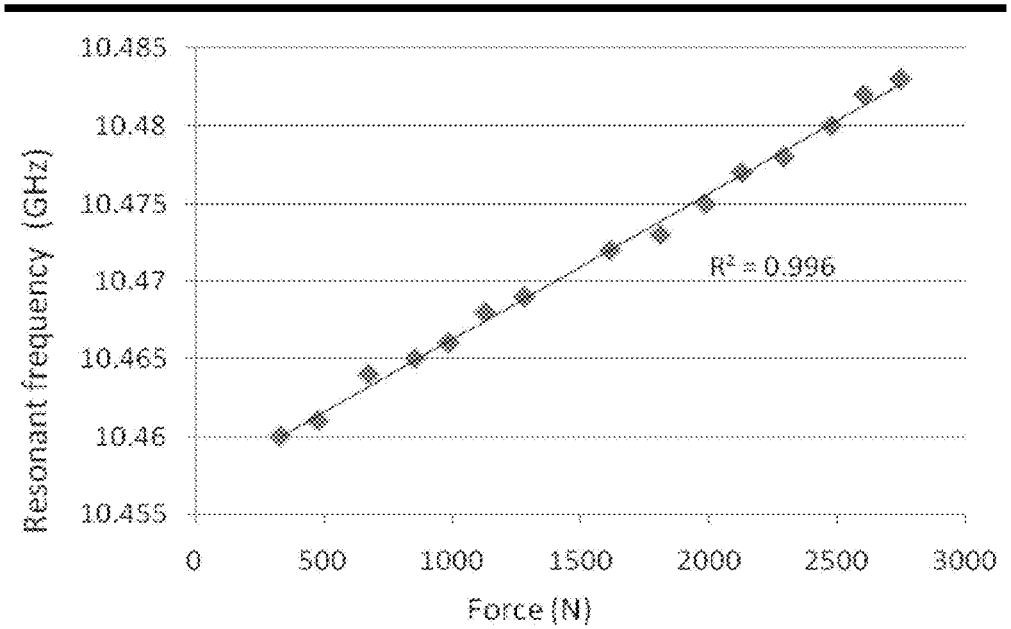
FIG. 49 illustrates resonant frequency as a function of load.

FIG. 49 illustrates the resonant frequency as a function of load. Such load can be appropriate to represent physiological loads. FIG. 49 demonstrates that a resonant frequency shift is detectable at loads as low as 333 N, which is less than half of an average body weight, and that the sensor response is extremely linear ($r^2$=0.996) in the 333N-2750N force range.

In various embodiments, a biocompatible resonator, which can be used as a bio-MEMS sensor, can include silicon as the substrate with gold used as the metal layer for the coil. Biocompatible silicon nitride ($Si_3N_4$) as a dielectric thin film of the resonator features a low loss tangent (as low as $5\times10^{-4}$) and a high dielectric constant (as high as 8) in the microwave frequency range. The low loss tangent significantly decreases the loss, whereas the high dielectric constant increases the dielectric film capacitance. Increasing both the metal width (w) and the spacing between metal lines (s) increases the Q-factor of the inductor ($Q_{ind}$), but also both increase the lateral area occupied on the substrate chip. These two parameters are selected to design towards optimization to obtain a highest Q-factor for a smallest chip size.

High-Q factor is achieved by using the capacitance of the dielectric thin film between the coil and the substrate for on-chip tuning to obtain an all on-chip, small-size microwave resonator. By using the high dielectric capacitor instead of an external capacitor, a spiral inductor configuration for the coil can be utilized in a manner in which a cavity resonator would be used. Thus, a high Q-factor can be obtained, comparable to the results of cavity resonator studies, but without sacrificing small chip area. In various embodiments, a sensor can effectively combine two different approaches: a spiral inductor structure and cavity resonator design techniques. In addition, considering the factors that reduce the losses and enhance the Q-factor, the losses can be designed towards minimization with a Q-factor designed towards maximization at a selected resonance frequency, such as 7 GHz. Parameters for bio-implantable resonator sensors can be determined for various coil configurations such that the sensors have a resonance frequency other than 7 Ghz.

Figure 50:
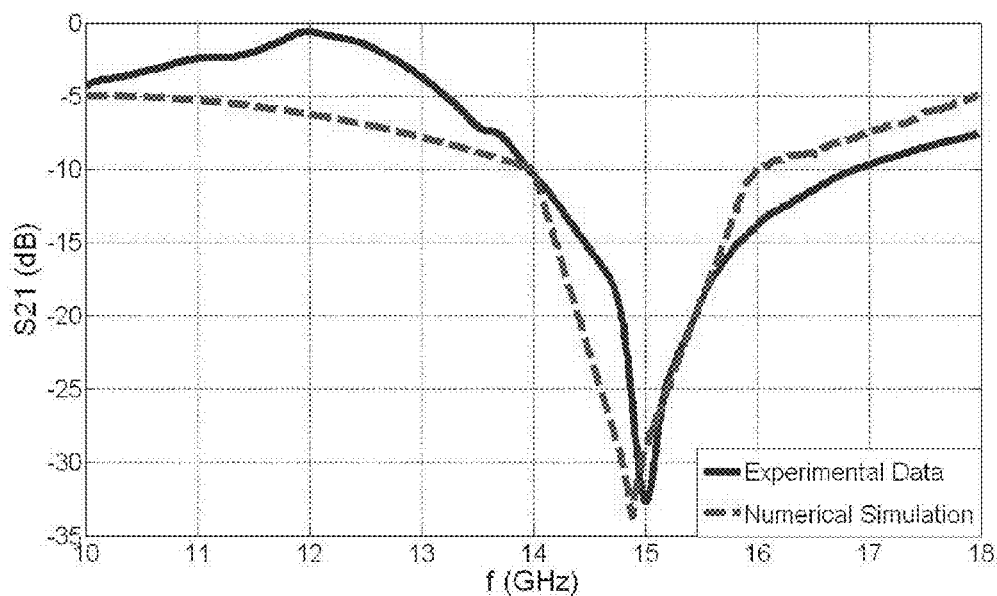
FIGS. 50-51 show experimentally measured $S_{21}$ parameter (in decibels) along with the numerically simulated parameter for a chip size of less than 200 square microns.
Figure 51:
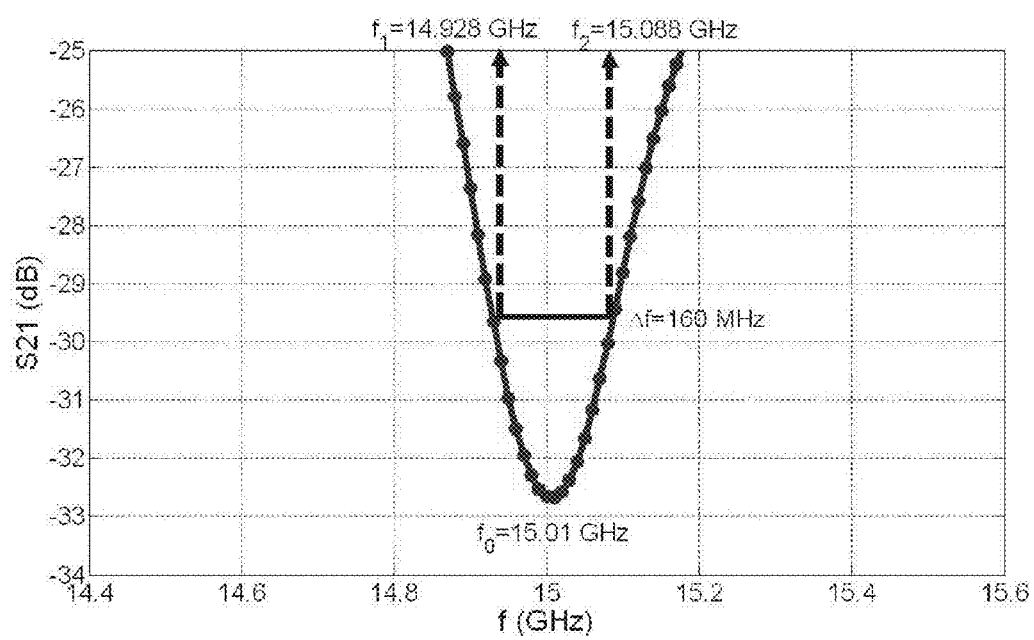

For a chip size of less than 200 square microns, FIGS. 50-51 show experimentally measured $S_{21}$ parameter (in decibels) along with the numerically simulated parameter. These Figs. show an excellent agreement between the experimental and theoretical results. In particular, there are matches between the experimental and theoretical resonance frequency ($f_0$) and the resonator Q-factor. Here, the resonator Q-factor is calculated from the experimental results by examining the dip in the transmitted power. The minimum point of $S_{21}$ is shown in the FIG. 50, which corresponds to $f_0$. A strong dip of greater than 30 dB in transmission is observed. To calculate the resonator Q-factor from the experimental data, those frequencies with $S_{21}$ parameters 3 dB above the resonance frequency are used. With respect to FIG. 51, $\Delta f$ is equal to 160 MHz, yielding a Q-factor of 93.81, in comparison to a theoretical Q-factor of 98.77. Both resonance frequencies are near 15 GHz. Theoretical calculations and experimental data are in good agreement. In various embodiments, a fully on-chip resonator can lead to a high Q-factor and a strong dip in transmission, such that the fully on-chip resonator can be used for telemetric-sensing applications.

In various embodiments, a suspended architecture for a resonator can be used, which helps increase the measured resonance frequency shift of the resonator. When a silicon substrate is used to fabricate the chip, it can be etched to obtain the suspended architecture. A wet etching process can be used to remove some of the substrate and dielectric. Other etching processes can be conducted. By etching the substrate, there is a decrease in the substrate loss. As a result, there is an increase in the silicon resistance ($R_{si}$) and decrease in the silicon capacitance ($C_{si}$). Hence, the overall result is an increase in the parallel resistance ($R_p$). By engineering a higher substrate loss factor, a higher Q-factor is obtainable. Due to the higher $R_{si}$ and lower $C_{si}$, there is a lower parallel capacitance ($C_p$); therefore a higher self resonance factor is obtained at the same frequency compared to the case with a single planar device. Thus, the resonance frequency is also higher. Combining these effects, both higher Q-factors and higher resonance frequencies are obtained with silicon removal.

By etching the substrate, there is also a higher shift of resonance frequency. This can be examined from two aspects. As a result of the etching of the substrate, the strain propagation is higher. Since the strain first occurs in the substrate then passes to the dielectric and metal layers, with an etched substrate, there is more strain and as a result there is more capacitance change. Hence, there is a higher $f_0$ shift. If the same load is applied to the single planar device and the single suspended device, assuming they have the same resonance frequency, then there is a higher shift of resonance frequency shift ($\Delta f_0$) in the single suspended device as a result of higher strain in dielectric and metal layer. Secondly, if there are two chips with same relative shift ($\Delta f_0/f_0$), the chip with the higher $f_0$ has the higher $\Delta f_0$ as well. Thus, the chip, with its etched substrate and with its higher $f_0$, also has a higher $\Delta f_0$.

In various embodiments, a triplet configuration can be used consisting of three sensors side-by-side. The individual sensors can be realized by any of the resonator structures discussed herein. The sensors on the outside act as the transmitter and receiver antennas for the middle sensor. Tables 3-6 show a comparison of four chips, a single configuration and a triplet configuration with both a planar architecture and a suspended architecture, with respect to resonance frequency (Table 3), resonance frequency shift (Table 4), Q-factor (Table 5), and sensitivity (Table 6).

TABLE 3

| | Load | | | |
|---|---|---|---|---|
| | No Load | 1960 N | 2940 N | 3920 N |
| Single Planar Device | 15.01 GHz | 15.30 GHz | 15.39 GHz | 15.44 GHz |
| Single Suspended Device | 15.18 GHz | 15.64 GHz | 15.83 GHz | 15.96 GHz |
| Planar Triplet | 15.06 GHz | 15.17 GHz | 15.23 GHz | 15.28 GHz |
| Suspended Triplet | 15.41 GHz | 15.56 GHz | 15.66 GHz | 15.75 GHz |

TABLE 4

| | Load | | |
|---|---|---|---|
| | 1960 N | 2940 N | 3920 N |
| Single Planar Device | 290 MHz | 380 MHz | 430 MHz |
| Single Suspended Device | 460 MHz | 650 MHz | 780 MHz |
| Planar Triplet | 110 MHz | 170 MHz | 220 MHz |
| Suspended Triplet | 150 MHz | 250 MHz | 340 MHz |

TABLE 5

| | Load | | | |
|---|---|---|---|---|
| | No Load | 1960 N | 2940 N | 3920 N |
| Single Planar Device | 93.81 MHz | 109.21 MHz | 110.96 MHz | 111.08 MHz |
| Single Suspended Device | 102.06 MHz | 116.54 MHz | 119.47 MHz | 120.02 MHz |
| Planar Triplet | 51.90 MHz | 57.38 MHz | 60.82 MHz | 62.55 MHz |
| Suspended Triplet | 67.15 MHz | 79.51 MHz | 80.31 MHz | 80.45 MHz |

TABLE 6

| | Sensitivity | Relative Shift |
|---|---|---|
| Single Planar Device | 0.1097 MHz/N | 2.9% |
| Single Suspended Device | 0.1990 MHz/N | 5.1% |
| Planar Triplet | 0.0561 MHz/N | 1.5% |
| Suspended Triplet | 0.0867 MHz/N | 2.2% |

In various embodiments, a circular architecture can be used, which gives an effectively reduced total area as compared to a rectangular geometry with the same overall dimensions. Thus, for a circular architecture, smaller film capacitance and coil inductance are attained, yielding a higher $f_0$. Also, there is lower coil resistance, lower loss, higher substrate resistance, and lower substrate capacitance for a circular architecture. This produces a higher substrate loss factor and higher self-resonance factor. As a result, with smaller spacing and higher $f_0$ in the circular geometry, a higher resonator Q-factor can be obtained.

The increase in the resonance frequency shift can be approached from two perspectives. First, the deformation is equally effective in any direction, due to isotropic geometry. However, in a rectangular geometry, there is a preferential, anisotropic deformation, which dominates unilaterally (effective on only one side at a time). In addition, the capacitance change in the circular case can be higher than that in the rectangular case with the same starting initial capacitance value because the deformation acts to change the whole geometry. Therefore, the associated resonance frequency shift can be larger. Next, even if there is an equal frequency shift ratio (relative shift), the frequency shift can be higher in the circular geometry, since it possesses a higher $f_0$. If these two aspects are combined, there can be a much higher shift for the circular case. Simulating $S_{21}$ parameters for the rectangular and circular devices and their triplet configurations, higher resonance frequencies and higher Q-factors for the circular geometry are also attained. Thus, better performance may be accomplished with the circular architecture.

Experimental results comparing the rectangular and circular geometries are shown in FIGS. 52-55. FIGS. 52-55 present $S_{21}$ (in dB) as a function of operating frequency for a single rectangular, a single circular, a triplet rectangular, and a triplet circular configuration, respectively. It can be seen, in the inset of each Fig., that the resonance frequency shift (to the right as viewed) can be much greater for the circular geometry in both configurations (single and triplet) than the rectangular. In the inset of each Fig., the resonance frequency at no load is lowest and the resonance frequency at the load of 3920 N is highest, with the resonance frequency at the loads of 1960 N and 2940 N shifting to the right respectively.

In Table 7, resonance frequency changes with respect to rectangular and circular geometries are presented. The resulting resonance frequency increase is higher for all of the circular device geometries. Since the area decrease is not linear and the capacitance is not linearly proportional to the resonance frequency, the resulting frequency increase is expectedly nonlinear. In addition, since the frequency shift is much higher in the circular cases compared to the rectangular cases, higher relative shift and higher sensitivity for the circular cases are observed in Table 7.

TABLE 7

| | | Load (N) | | | |
|---|---|---|---|---|---|
| | | No load | 1960 | 2940 | 3920 |
| | | | Microstrain | | |
| | | 0 | 81.5 | 127.7 | 172.8 |
| Single Rectangular | $f_0$ (GHz) | 11.48 | 11.72 | 11.78 | 11.81 |
| | $\Delta f_0$ (MHz) | — | 240 | 300 | 330 |
| | $\Delta f_0/f_0$ (%) | — | 2.1 | 2.6 | 2.9 |
| | Q-factor | 59.979 | 70.348 | 74.324 | 76.000 |
| | Sensitivity | 0.0842 MHz/N or 1.9 MHz/microstrain | | | |
| Single Circular | $f_0$ | 12.63 | 12.98 | 13.07 | 13.13 |
| | $\Delta f_0$ | — | 350 | 440 | 500 |
| | $\Delta f_0/f_0$ (%) | — | 2.8 | 3.5 | 4.0 |
| | Q-factor | 72.461 | 91.667 | 93.025 | 93.786 |
| | Sensitivity | 0.1276 MHz/N or 2.9 MHz/microstrain | | | |

TABLE 7-continued

| | | Load (N) | | | |
|---|---|---|---|---|---|
| | | No load | 1960 | 2940 | 3920 |
| | | | Microstrain | | |
| | | 0 | 81.5 | 127.7 | 172.8 |
| Triplet Rectangular | $f_0$ | 11.56 | 11.66 | 11.71 | 11.73 |
| | $\Delta f_0$ | — | 100 | 150 | 170 |
| | $\Delta f_0/f_0$ (%) | — | 0.9 | 1.3 | 1.5 |
| | Q-factor | 33.801 | 36.347 | 38.243 | 39.231 |
| | Sensitivity | 0.0434 MHz/N or 1.0 MHz/microstrain | | | |
| Triplet Circular | $f_0$ | 12.73 | 12.86 | 12.93 | 12.99 |
| | $\Delta f_0$ | — | 130 | 200 | 260 |
| | $\Delta f_0/f_0$ (%) | — | 1.0 | 1.6 | 2.0 |
| | Q-factor | 44.033 | 50.431 | 53.364 | 55.442 |
| | Sensitivity | 0.063 MHz/N or 1.5 MHz/microstrain | | | |

Table 7 also provides Q-factor data, which are observed to be high despite the relatively small chip sizes. These Q-factors are particularly higher in the circular case with a smaller area. The Q-factor is increased as the load magnitude is increased due to a lower $C_{film}$. The Q-factor also increases for the telemetric case (triplet) of the circular case compared to the rectangular case.

In various embodiments, a strain sensor can be realized by a metamaterial-based RF-MEMS strain sensor that is highly sensitive to mechanical deformation. Using split-ring-resonators, lower resonance frequencies per unit area can be achieved compared to other RF structures, allowing for bio-implant sensing in soft tissue applications, which include fracture healing. In a 5×5 SRR architecture, the wireless sensors yield high sensitivity with low nonlinearity-error.

A SRR geometry can be more sensitive compared to the spiral case because of its additional gaps. These gaps can produce additional capacitance, which is changed when the load is applied. Hence, it makes SRR more sensitive than a spiral coil geometry. In addition, the electric field density is much higher in the gaps, so these gaps are important to obtain strong resonances. When the load is applied, these gaps change and hence the resonance frequency changes. This leads to higher sensitivity in SRRs compared to a spiral coil structure. Also, as a result of these gaps, SRRs yield higher dips and higher Q-factors compared to the spiral structure. This enables telemetric measurement and observation of the resonance frequency more easily. As a result, the SRR sensor can have increased linearity over that of the spiral coil sensor. Also, because of these gaps, there are lower resonance frequencies per unit area, which is useful for bio-implantation applications. Therefore, because of the gaps in the SRR structure, there can be a higher Q-factor, higher dip, higher sensitivity, better linearity, and lower resonance frequency per unit area compared to the spiral coil structure.

Figure 56:
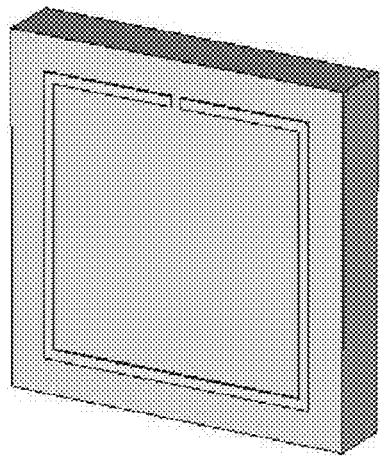
FIGS. 56-60 illustrate different split ring resonators.
Figure 57:
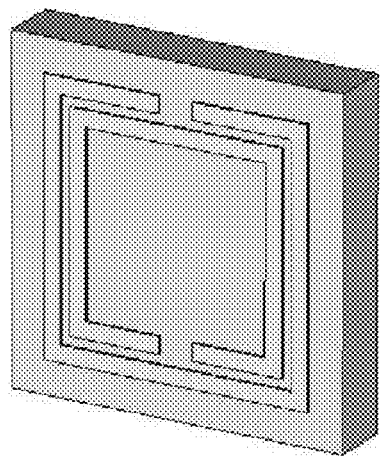
Figure 58:
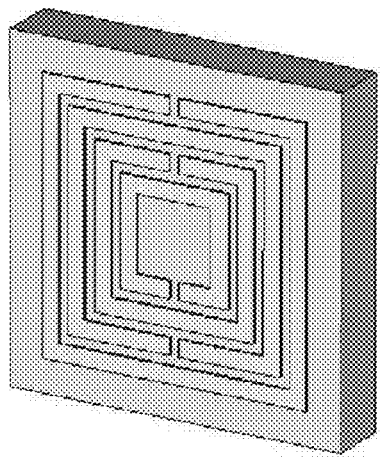
Figure 59:
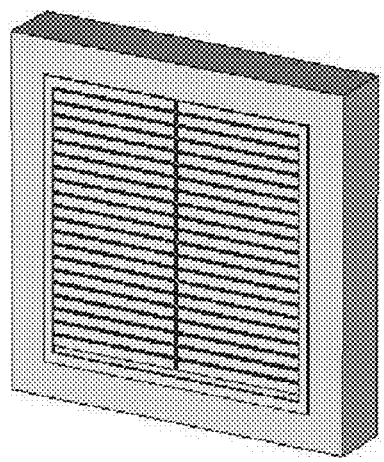
Figure 60:
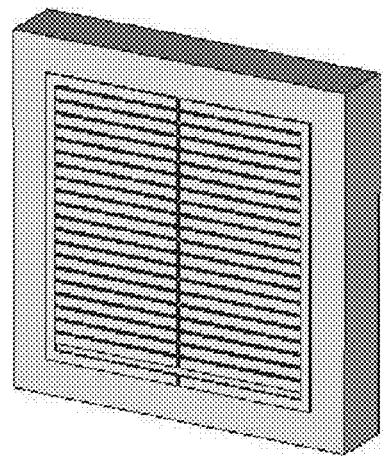

FIGS. 56-60 illustrate different split ring resonators. FIG. 56 shows a one turn SRR. FIG. 57 shows a SRR with two turns. FIG. 58 shows a SRR with four turns. FIG. 59 shows a nested SRR architecture. FIG. 60 shows a SRR having a comb-like structure.

These SRR structures can be combined to form compact nested metamaterial-based strain sensors on a single chip to achieve significantly enhanced sensitivity in telemetric sensing. This architecture features substantially more gaps compared to the structure of a non-nested SRR. This decreases the operating resonance frequency of the resulting nested SRR sensor compared to a non-nested SRR sensor. Moreover, when the external load is applied to hardware the capacitance of the nested SRR sensor can be changed more than the non-nested SRR, resulting in larger shifts in the transmission spectrum. This can make the nested SRR more sensitive than non-nested SRR for sensing.

Figure 61:
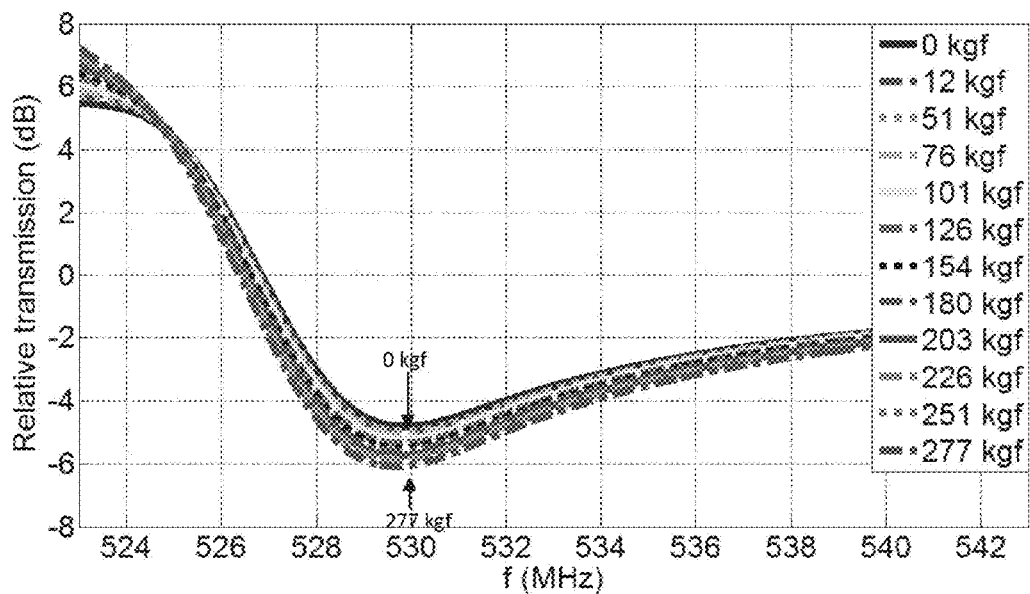
FIGS. 61-63 show different sets of relative transmission spectra (in dB) for non-nested split ring resonators.
Figure 62:
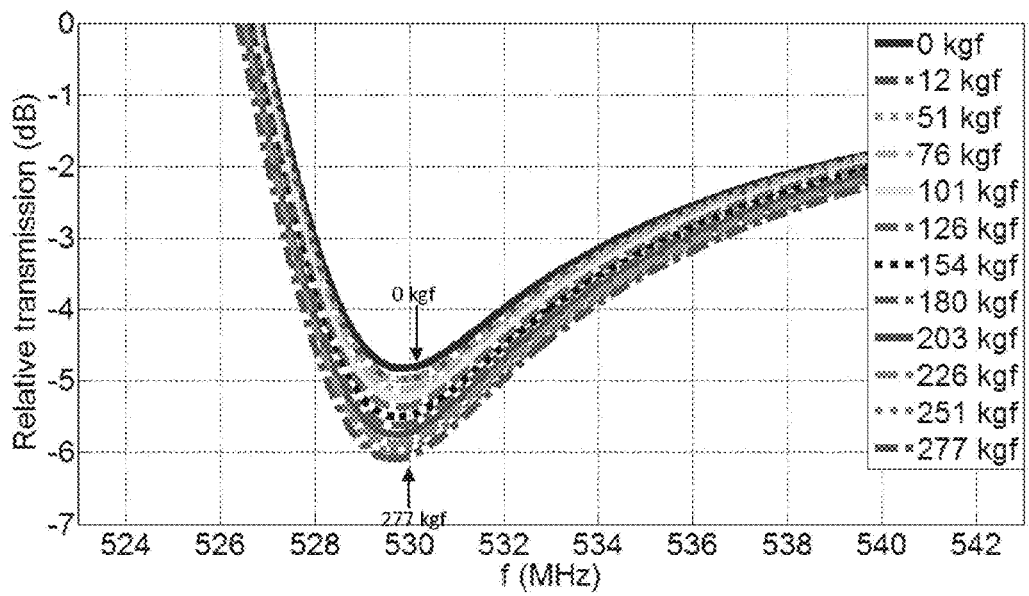
Figure 63:
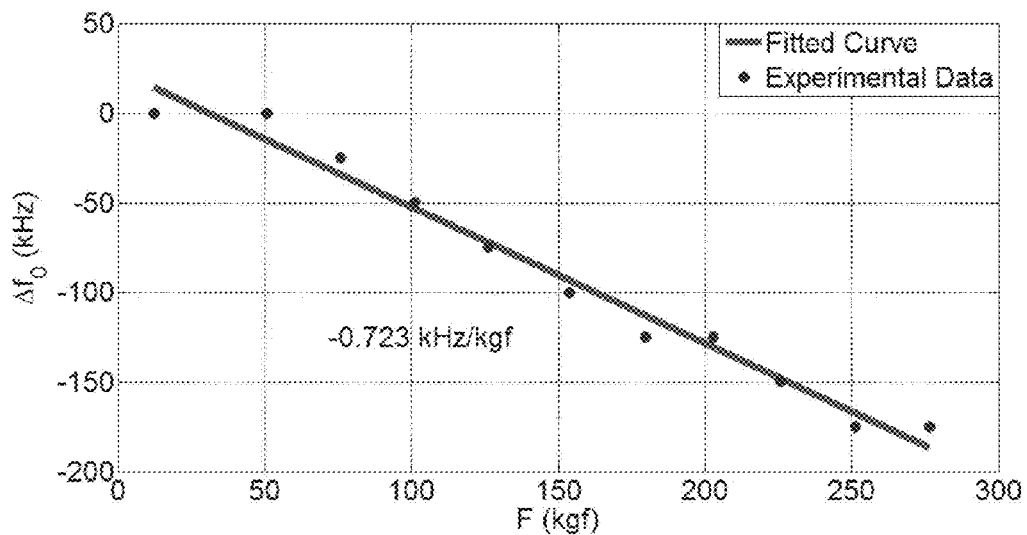

In FIGS. 61-63 and FIGS. 64-66, different sets of relative transmission spectra (in dB) are presented for the non-nested SRR and nested SRR sensors, respectively, with respect to the case of no sensor on semi-log scale. FIG. 61 shows the relative transmission spectra of the non-nested SRR under different levels of the applied load, whereas FIG. 62 zooms into the transmission shift that is observed with the applied load. Under no load, the operating frequency is approximately 530 MHz. With the applied load, the operating frequency decreases as seen in FIGS. 61 and 62. Under the applied load, the capacitance is increased. FIG. 63 illustrates the operating frequency shift vs. the applied load.

Figure 64:
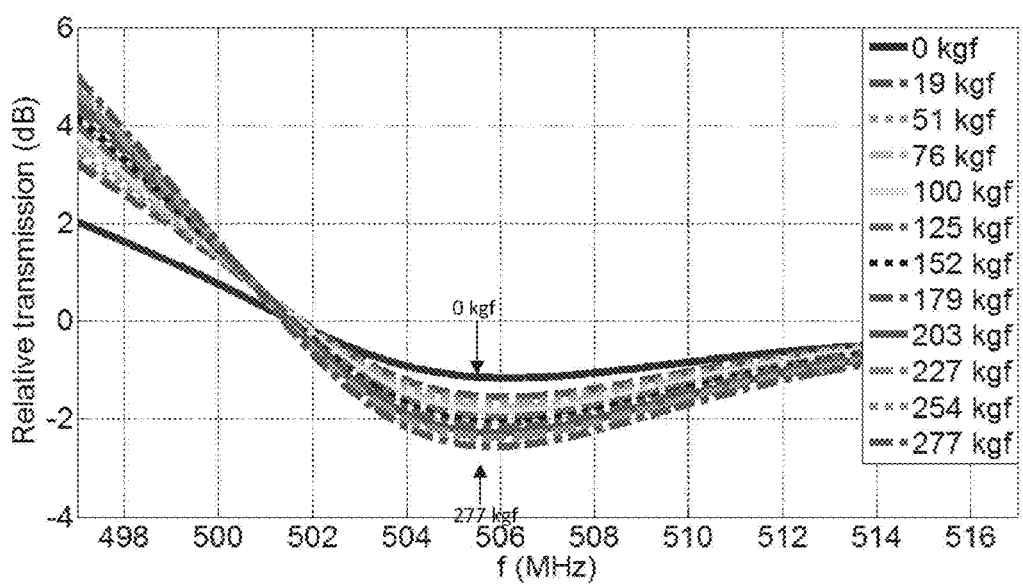
FIGS. 64-66 show different sets of relative transmission spectra (in dB) for nested split ring resonators.
Figure 65:
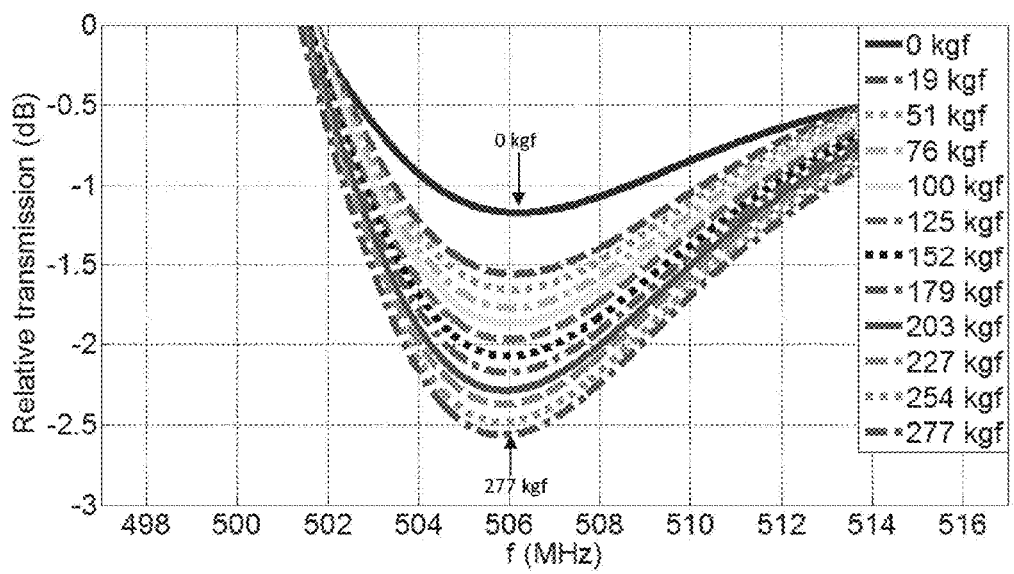
Figure 66:
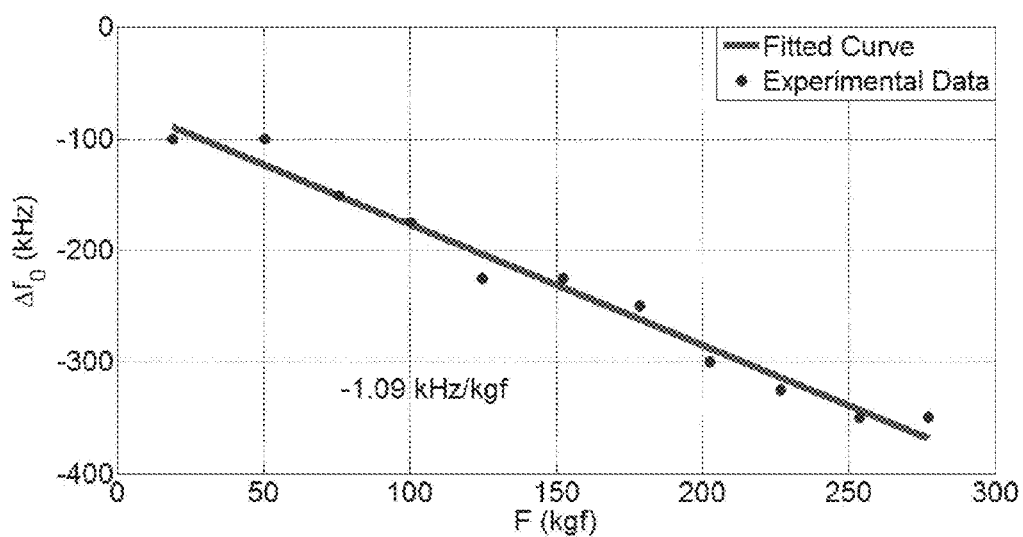

FIG. 64 shows the transmission spectra of the nested SRR structure for different levels of the applied load, with their zoomed transmission shifts in FIG. 65. Here the operating frequency is significantly less than the non-nested SRR under no load. FIG. 66 plots the change in the operating frequency as a function of the applied load. The sensitivity of the nested SRR (FIG. 66) can be significantly increased compared to the non-nested SRR (FIG. 63) as a result of the multiple gaps used in the nested SRR.

A sensor using silicon, silicon nitride, and gold have been shown to be biocompatible, as the result of a study using New Zealand White Rabbits. It produces no tissue reaction after being implanted in these animals for six months. The tissue surrounding and overlying the implant, both for the sensor material and the $Al_2O_3$ control material, was macroscopically evaluated for evidence of internal and external lesions in accordance with a semi-quantitative scoring system. Each implant was then removed with an intact envelope of surrounding tissue and fixed for 24 hours in 10% neutral buffered formalin. After fixation, each implant was removed from the tissue envelope and the tissue specimens were routinely processed, embedded in paraffin, sectioned, and stained with Hematoxylin and Eosin (H&E) for semi-quantitative evaluation of the cellular and tissue response to the sensor and control materials. Microscopic evaluation was performed by a single board certified pathologist who was blinded to the treatment groups so as to avoid observer bias.

Figure 67:
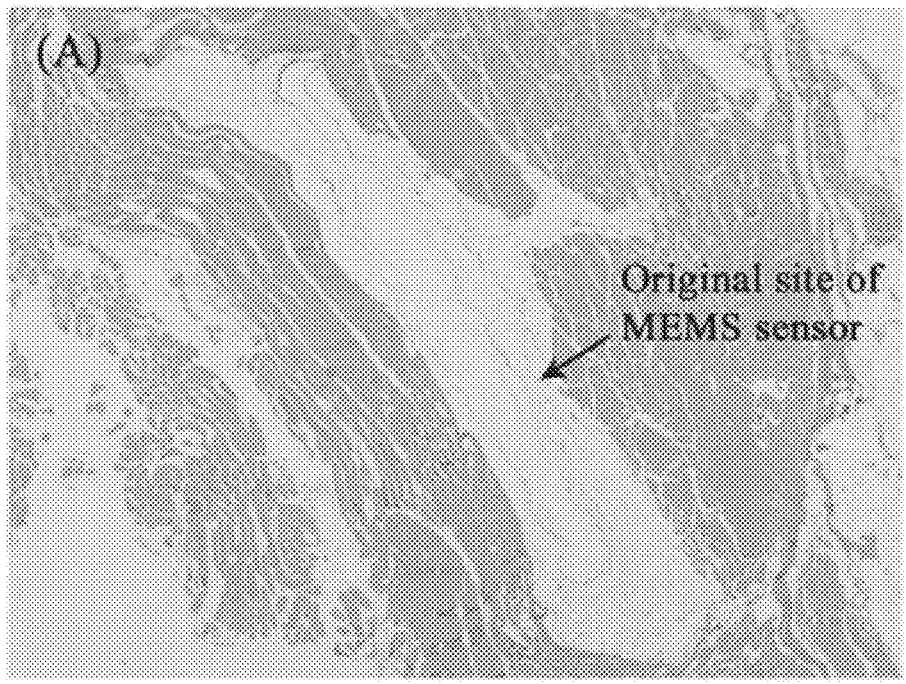
FIGS. 67-68 show 2× and 4× images of H&E stained tissue adjacent to an implanted MEMS sensor.
Figure 68:
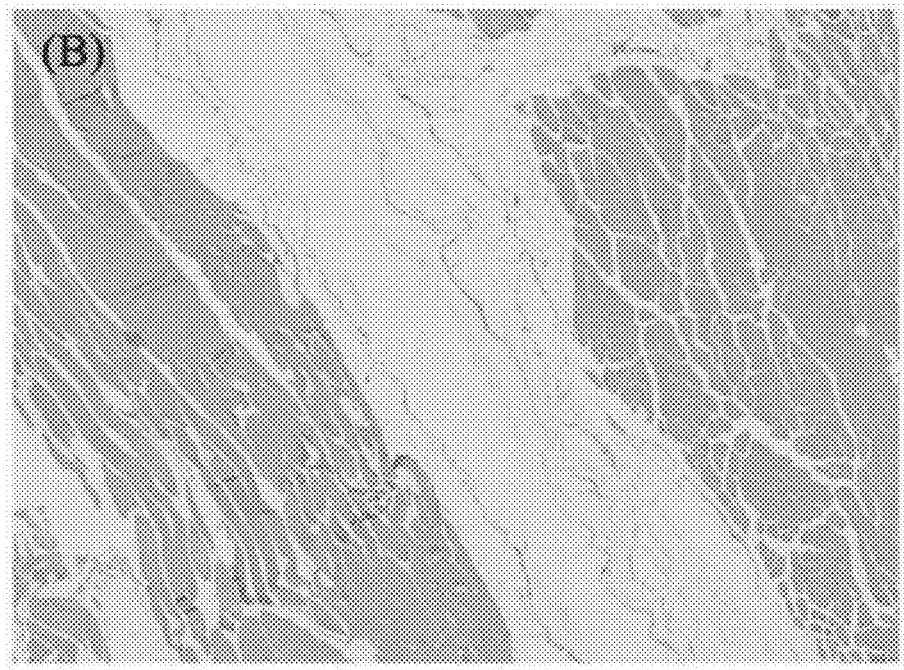

During convalescence, there were no complications resulting from the surgical procedure, no evidence of post-operative infection, and no mortality in the six-month survival period. Gross examination of tissue adjacent to these sensor materials did not reveal any visible signs of adverse reactions manifested as external or internal lesions to the test materials. No infection or inflammation was grossly noted in the musculature surrounding implanted materials. Examination of histological slides confirmed the absence of abnormal macrophage or lymphocytic cellular activity, and the general toxicity score for the test and control materials was zero. FIGS. 67 and 68 show 2× and 4× images of H&E stained tissue adjacent to implanted MEMS sensor.

The sensor is shown to perform well in the presence of soft tissue filling up the space between the antennas and the sensor. In the soft tissue, the operating frequency is about 475 MHz under no load, which is lower than the nested SRR in free space. This is because the soft tissue has a very high dielectric constant around 500 MHz, and this decreases the resonance frequency. The nested SRR sensor can also present a high sensitivity level of 4 kHz/kgf, since the soft tissue better focuses electromagnetic waves compared to the free space because of its high dielectric constant at low frequencies. As a result, the mechanical deformation under load affects the operating frequency more strongly, which leads to better sensitivity in the soft tissue.

The sensors were designed and tested approximately in the range of 100 MHz to 6 GHz resonance frequencies at no load. It is desirable to operate in the low to middle MHz range for use in a biological environment. Moreover, it is further desirable to fabricate sensor providing 50 MHz to 2 GHz resonance frequencies at no load for the physiological applications. If the natural frequency is too high, such as 6 GHz, while the RF signal (loaded or unloaded) from the sensor is detectable when the sensor is not implanted, the RF signal is not detectable (loaded or unloaded) because the signal will be lost in the body tissues at this operating frequency. If the operating frequency is in the low to middle MHz range then the signal (and resultant shift in the signal with loading) is easily detectable. Lowering the operating resonance frequency lowers the background absorption of soft tissue while increasing penetration depth. Depending on the penetration depth required to receive a sufficient signal from the sensor in the soft tissue, the operating resonance frequency range can be the sub-GHz, and perhaps even in the low GHz. As the operating resonance frequency is further lowered, the background loss can be reduced further. But this comes at the cost of increasing the size of the sensor to be able to operate at such low frequency. In this respect, the desirable operating range can go below 100 MHz, preferably to 50 MHz. The physiological load range can range from 0-3000N (3000 being approximately 4× the average person's body weight of 750N).

The soft tissue medium is advantageous for the sensing application, since the operating frequency is lowered. In various embodiments, large spacing between the soft tissue and the antennae of the sensor are avoided. If there is sufficient free space between the soft tissue and the antennae, then the antenna signal decreases.

Using a flexible substrate, such as a vacuum tape, can provide higher sensitivity and linearity for a wireless sensor, as compared to using silicon substrate. A difference in the fabrication procedure between the tape-based flexible sensor and the silicon-based sensor includes the deposition of a first gold layer onto the vacuum tape substrate. The first gold layer increases the absorption of the sensor at the resonance frequency, so that there is a high dip at the resonance frequency. However, with silicon substrate, the silicon itself increases absorption without an extra gold layer. Deposition of the first gold layer also forms the parallel plate capacitor with the dielectric between the first and final gold layers of the tape-based flexible sensor. For the silicon-based sensor, a parallel plate capacitor can be formed without an extra gold layer, since a doped silicon substrate can be used. In addition, for the silicon-based sensor, hard epoxy can be used to fix the sensor to the hardware. For the tape-based flexible sensor, no external epoxy is needed because the tape has its own epoxy or other fixation material.

Figure 69:
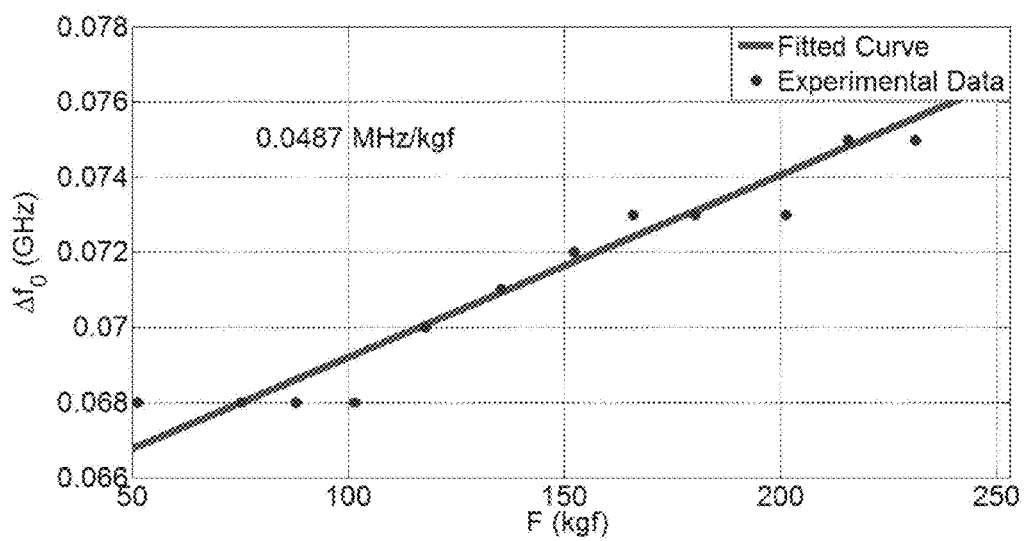
FIG. 69 shows the performance of a silicon-based sensor.
Figure 70:
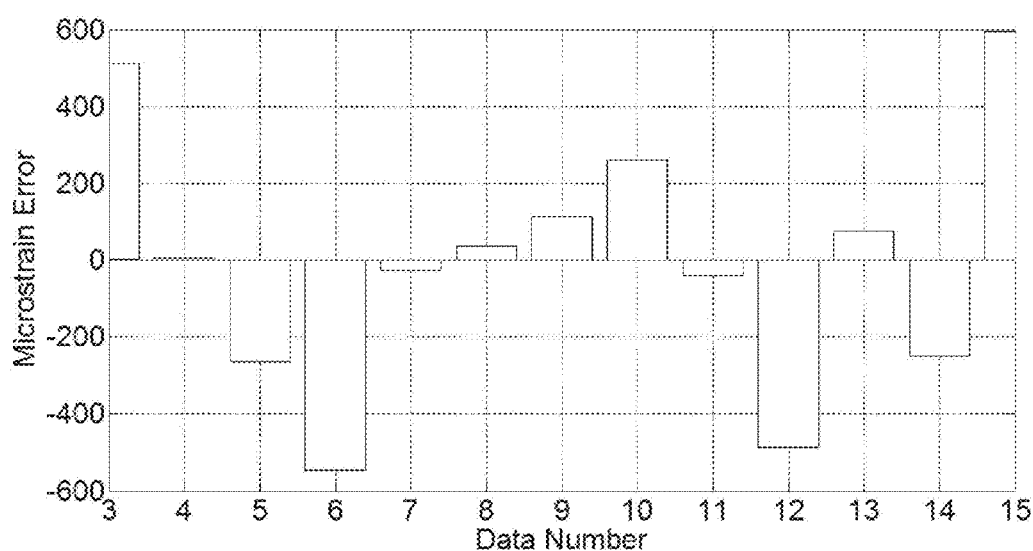
FIGS. 70-71 show the nonlinearity-error for the silicon-based sensor of corresponding to FIG. 69.
Figure 71:
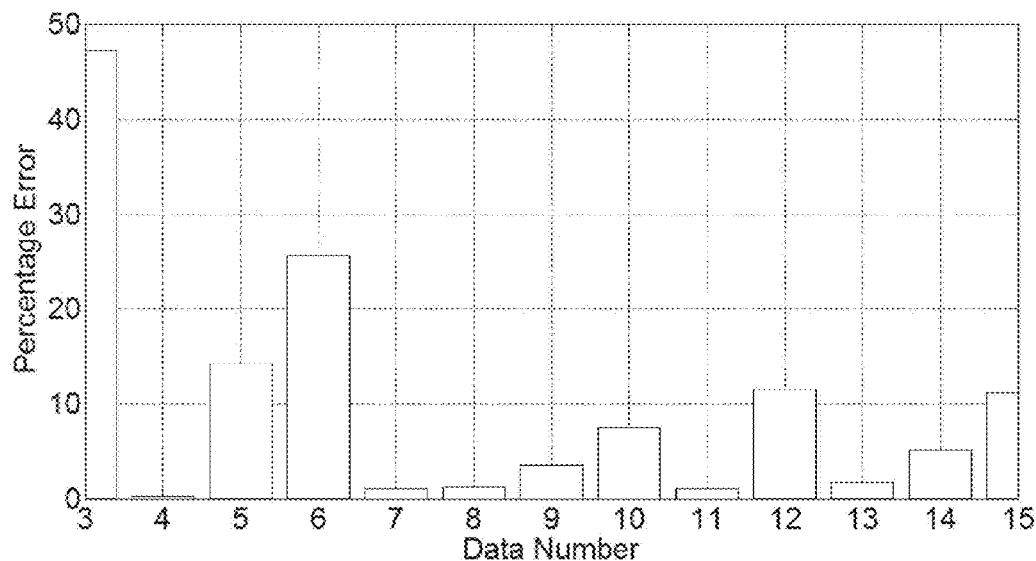

FIGS. 69-70 shows the performance of a silicon-based sensor, which demonstrates over 10 dB transmission dip in all cases of the strain examined. The sensitivity is shown in FIG. 69. In this Fig., $\Delta f_0$ is used as the shift of resonance frequency with respect to no load resonance frequency and F is used as the applied force. FIGS. 70 and 71 show the nonlinearity-error.

Figure 72:
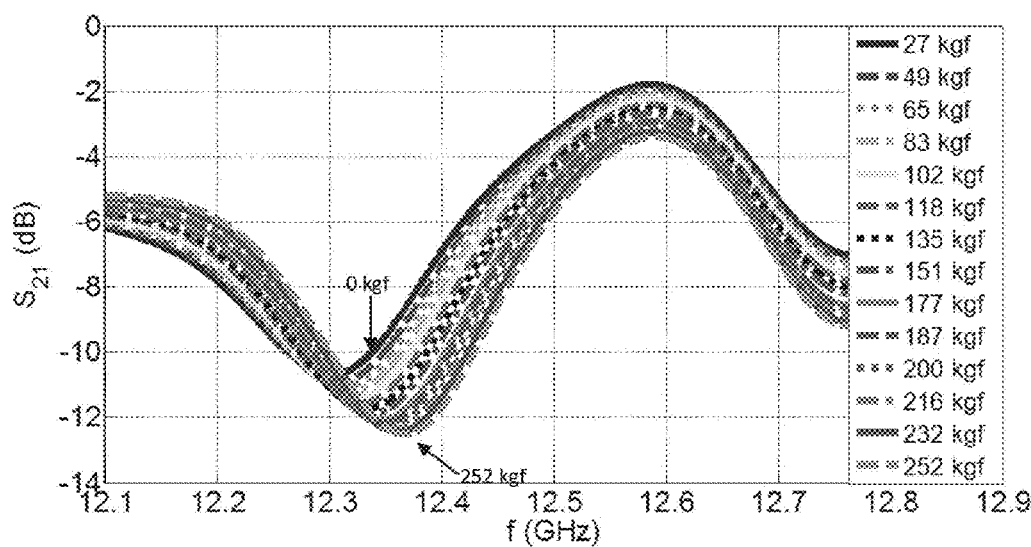
FIGS. 72-76 shows the performance of a tape-based flexible sensor.
Figure 73:
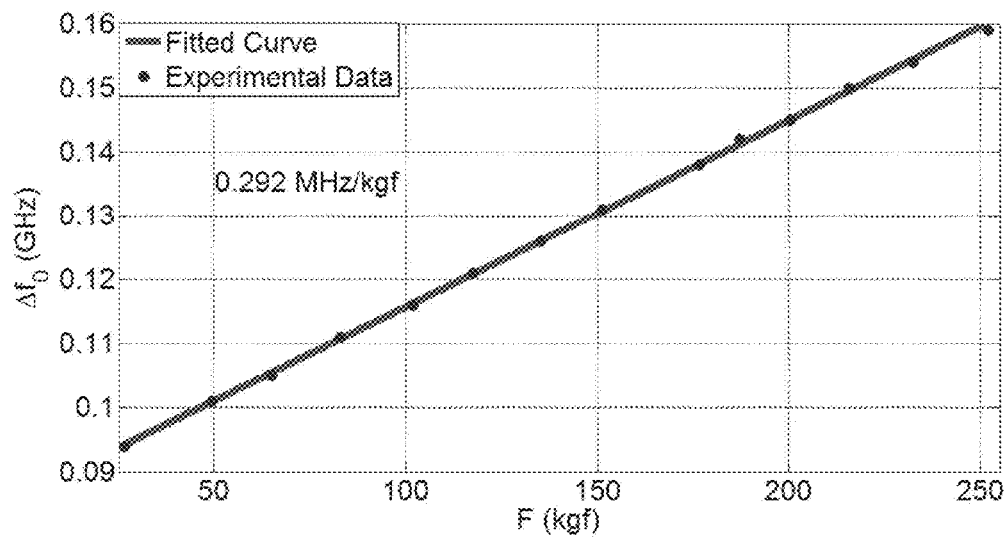
Figure 74:
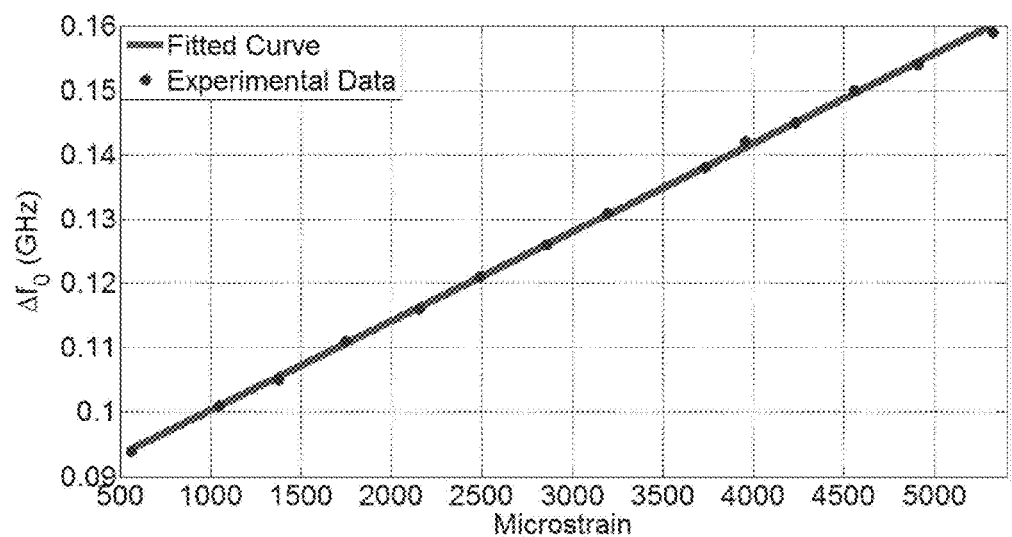
Figure 75:
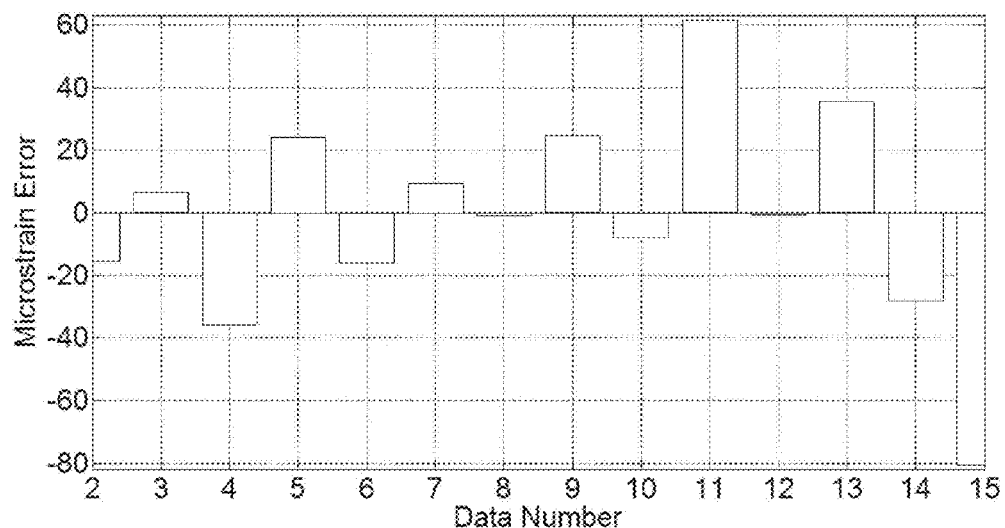
Figure 76:
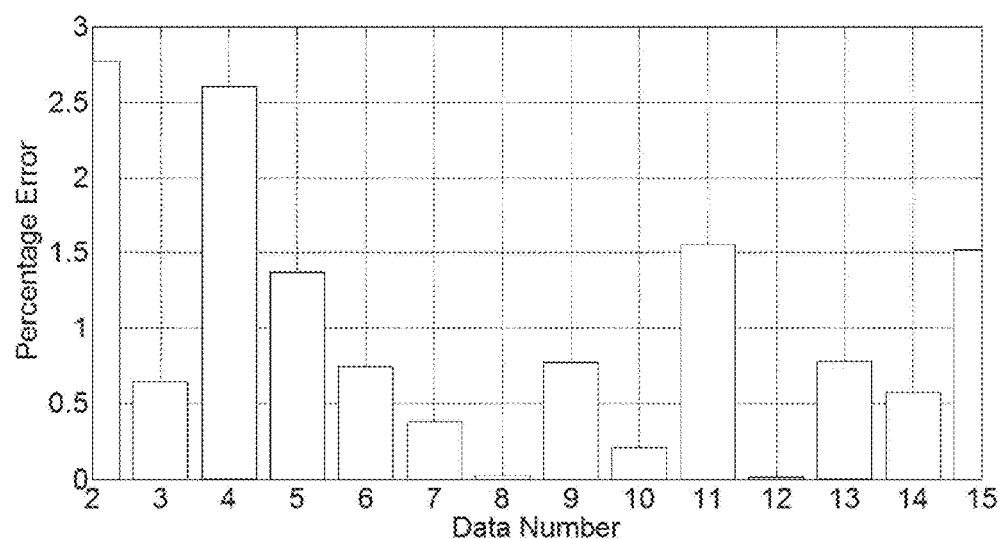

FIG. 72 shows $S_{21}$ parameters of the tape-based flexible sensor, which shows more than 10 dB dip in transmission spectra for the different cases of the strain examined. FIG. 73 shows a graph of $\Delta f_0$ versus F. Then, using the Young's modulus of the cast polyamide test stick used as hardware, the microstrain is determined and plotted vs $\Delta f_0$ in FIG. 74. There is less than 80 microstrain nonlinearity-error as shown in FIG. 75 and less than 3% nonlinearity-error as can be seen in FIG. 76. Overall, there can be better sensitivity and better linearity in the tape-based flexible sensor compared to the silicon-based sensor.

In various embodiments, an inductively-powered wireless sensor can be used to monitor strain on hardware that is implanted in the body. An inductively-powered wireless sensor, with a lateral area of less than 1 $cm^2$, can operate at resonance frequencies around 500 MHz. Such a sensor can have a sensitivity of up to 4 kHz/kgf in the presence of soft tissue. In various embodiments, an inductively-powered wireless sensor can be constructed of materials that are biocompatible, which makes this sensor an excellent bio-MEMS device.

Figure 77:
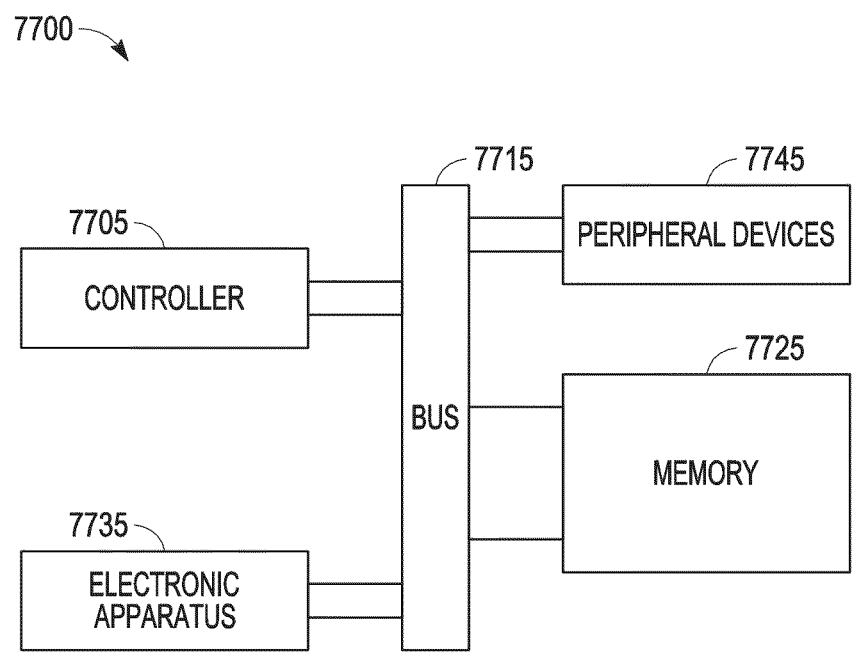
FIG. 77 shows a block diagram of various features of an embodiment of a system.

FIG. 77 shows a block diagram of various features of an embodiment of a system 7700. System 7700 can be configured to control the probing of an inductively powered sensor implanted in a biological subject, such as a person. This controlled probing can be used to monitor changes in strain in hardware implanted in the subject, where the hardware has the sensor attached thereto. As a fracture in a person heals, an implanted plate, to aid in the healing process, is subjected to less stress, with subsequent changes in strain in the hardware. With changes in hardware strain, there are changes to the capacitive structure of the sensor, which is exhibited by a shift in resonant frequency of a resonator or resonators of the sensor. System 7700 can be used to regulate excitation of the sensor over time, to direct the collection of resonant frequency data, to store relevant data including appropriate parameters, calibration data, and collected data, and to analyze the collected resonant frequency data with respect to changes in load supported by the hardware and load supported by the healing bone of the fracture. System 7700 can include monitoring system of FIG. 19.

System 7700 can include a controller 7705, bus 7715, memory 7725, an apparatus 7735, and peripheral devices 7745. System 7700 can be formed in various ways such as coupling the individual components of system 7700 together or integrating the components into one or a number of units using conventional techniques. Bus 7715, can provide electrical conductivity between the various components of system 7700. In an embodiment, bus 7715 includes an address bus, a data bus, and a control bus, each independently configured. In an alternative embodiment, bus 7715 uses common conductive lines for providing one or more of address, data, or control, the use of which is regulated by controller 7705.

Apparatus 7735 can include probes for generating electromagnetic stimuli to the sensor on the hardware implanted in a subject. The stimuli can power on the sensor. Apparatus 7735 can also include receivers to receive the electromagnetic signals from the sensor in response to the stimuli. Apparatus 7735 can include circuitry to determine the resonant frequency of the signal received from the sensor. The sensor may be realized in accordance with various embodiments described herein.

Memory 7725 can include any form of memory having the capacity to store and receive data and to store and receive instructions for operation of system 7700. Memory 7725 can include, but are not limited to, magnetic memory, removable memory, and all forms of semiconductor-based memory. Memory 7725 can be arranged as a machine-readable medium that stores instructions, which, when performed by system 7700, cause system 7700 to perform operations to manage the monitoring and analysis of the healing of a fracture of a subject. The instructions can be processed by controller 7705. In an embodiment, controller 7705 includes a processor.

In various embodiments, peripheral device or devices 7745 are coupled to bus 7715. Peripheral devices 7745 may include keyboards, displays, imaging devices, printing devices, wireless devices, wireless interfaces (e.g. wireless transceivers), additional storage memory, and control devices that may operate in conjunction with controller 7705 or other components of system 7700.

Bus 7715 can also include or be connected to a communication interface, such as an ethernet, a USB, or a Firewire, which can be used to communicate with the electronic network for connecting to an electronic network, public network, such as the Internet, or private network, such as a corporate Local Area Network (LAN) or Wide Area Network (WAN), or a virtual private network. Other computer systems can also be linked to this system for enabling remote monitoring, observing, and even analyzing the results obtained from the sensor. A wireless communication system can also be used.

Furthermore, it should be recognized that the system and network disclosed herein can be programmed and configured, by one skilled in the art, to implement the methods, system, and software discussed further herein, as well as provide requisite computer data and electronic signals to implement the present invention.

Although specific embodiments have been illustrated and described herein with reference to exemplary embodiments relating to implantable hardware, it will be appreciated by those of ordinary skill in the art that the foregoing embodiments and techniques can be used for other monitoring or diagnostic purposes, such as detecting stress in structures. All modifications and equivalents attainable by one of ordinary skill in the art from the present disclosure within the scope and spirit of the present invention are to be included as further embodiments of the present invention. It is to be understood that the above description is intended to be illustrative, and not restrictive, and that the phraseology or terminology employed herein is for the purpose of description. The scope of the present accordingly is to be defined as set forth in the appended claims.

What is claimed is:

1. A method of monitoring changes in a hardware implant device using a sensor device mounted to or integrated with the hardware device, which is implanted in a subject,
    wherein the sensor device comprises:
    a substrate; and
    a resonator configured as a strain gauge composed essentially of:
        a solid dielectric material disposed over the substrate as a dielectric capacitor;
        a conductive layer between the substrate and the solid dielectric material and in contact with the substrate and the solid dielectric material; and
        at least one conductive coil disposed on the solid dielectric material,
    wherein the substrate, the conductive layer, the solid dielectric material, and the conductive coil are configured to undergo strain as the hardware implant device mounted to or integral with the sensor device undergoes strain,
    wherein the substrate, the conductive layer, the solid dielectric material, and the conductive coil are configured as a biocompatible sensor device for implantation in a biological subject,
    wherein the resonator is configured to be inductively powered without an incorporated power supply, wherein the resonator is configured to reflect electromagnetic waves corresponding to a resonant frequency of the resonator in response to an alternating magnetic or electromagnetic field directed toward the sensor device, and wherein the resonant frequency of the resonator shifts in correspondence with strain applied to the resonator by the hardware implant device, wherein the method comprises the steps of:

inductively powering the resonator by directing an alternating magnetic or electromagnetic field toward the sensor device at different times over a period;

receiving electromagnetic waves reflected from the resonator, which undergoes strain as the hardware implant device undergoes strain, at different times over the period;

determining a shift in a resonant frequency of the resonator based on the received reflected electromagnetic waves at different times over the period; and determining a temporal change in strain of the hardware implant device based on the determined shift in the resonant frequency of the resonator over the period.

2. The method of claim 1, wherein the hardware implant device is implanted in a biological subject.

3. The method of claim 2, wherein:

the resonant frequency determining step determines the resonant frequency of the resonator by inputting the received signals to a spectrum analyzer, and the resonator is configured to have a resonant frequency ranging from 50 MHz to 7 GHz at no load.

4. The method of claim 2, further including the step of determining a change in the biological subject based on the temporal change in strain of the hardware implant device.

5. The method of claim 2, wherein the temporal change in strain of the hardware implant device is determined using a strain-frequency calibration of the hardware implant device.

6. The method of claim 2, further including the step of monitoring surface bending strains of the hardware implant device.

7. The method of claim 2, wherein the hardware implant device includes a fracture fixation plate and the sensor device is attached to a surface of the fracture fixation plate.

8. A sensor device mountable to or integral with a hardware implant device, which is implantable in a subject, for monitoring strain applied to the hardware implant device, the sensor device comprising:

a substrate; and a resonator configured as a strain gauge composed essentially of:

a solid dielectric material disposed over the substrate as a dielectric capacitor;

a conductive layer between the substrate and the solid dielectric material and in contact with the substrate and the solid dielectric material; and at least one conductive coil disposed on the solid dielectric material, wherein the substrate, the conductive layer, the solid dielectric material, and the conductive coil are configured to undergo strain as the hardware implant device mounted to or integral with the sensor device undergoes strain, wherein the substrate, the conductive layer, the solid dielectric material, and the conductive coil are configured as a biocompatible sensor device for implantation in a biological subject, wherein the resonator is configured to be inductively powered without an incorporated power supply, wherein the resonator is configured to reflect electromagnetic waves corresponding to a resonant frequency of the resonator in response to an alternating magnetic or electromagnetic field directed toward the sensor device, and wherein the resonant frequency of the resonator shifts in correspondence with strain applied to the resonator by the hardware implant device.

9. The sensor device of claim 8, wherein the substrate is flexible.

10. The sensor device of claim 9, wherein the flexible substrate is configured as a flexible tape.

11. The sensor device of claim 8, wherein the solid dielectric material is composed of silicon nitride and the conductive coil is composed of gold.

12. The sensor device of claim 8, wherein the resonator is composed of a metamaterial.

13. The sensor device of claim 8, wherein the conductive coil has one of a spiral, split-ring, or nested split-ring configuration.

14. The sensor device of claim 13, wherein the spiral configuration has a continuous length of conductive material with at least two spiral turns.

15. The sensor device of claim 13, wherein the nested split-ring configuration includes an inner square and an outer square, the outer square including a first break and the inner square including a second break, the first break being along a length of the outer square that is opposite a length of the inner square having the second break.

16. The sensor device of claim 15, further including an array of nested split-ring configuration.

17. The sensor device of claim 13, wherein the spiral coil configuration has at least two spiral turns.

18. The sensor device of claim 13, wherein the nested split-ring configuration has a plurality of rectangles with a common base side but having different heights, and each having a gap opposite the base side.

19. The sensor device of claim 8, further including an array of conductive coils.

20. The sensor device of claim 19, wherein the array of conductive coils includes at least two different coil configurations.

21. The sensor device of claim 8, wherein the resonator has a suspended resonator structure.

22. The sensor device of claim 8, wherein the conductive coil includes a triplet configuration and each of the triplet configuration is one of a rectangular spiral coil resonator, a circular spiral coil resonator, a suspended resonator, or a split-ring-resonator.

23. The sensor device of claim 8, wherein the resonator is configured to have a resonant frequency ranging from 50 MHz to 7 GHz at no load.

24. An apparatus implantable in a biological subject, the apparatus comprising:

a hardware implant device; and a sensor device attached to or integrated with the hardware implant device, wherein the sensor device includes:

a substrate; and a resonator configured as a strain gauge composed essentially of:

a solid dielectric material disposed over the substrate as a dielectric capacitor;

a conductive layer between the substrate and the dielectric material and in contact with the substrate and the dielectric material; and at least one conductive coil disposed on the solid dielectric material, wherein the substrate, the conductive layer, the solid dielectric material, and the conductive coil are configured to undergo strain as the hardware implant device mounted to or integral with the sensor device undergoes strain, wherein the substrate, the conductive layer, the solid dielectric material, and the conductive coil are configured as a biocompatible sensor device for implantation in a biological subject, wherein the resonator is configured to be inductively powered without an incorporated power supply, wherein the resonator is configured to reflect electromagnetic waves corresponding to a resonant frequency of the resonator in response to an alternating or electromagnetic field directed toward the sensor device, and wherein the resonant frequency of the resonator shifts in correspondence with strain applied to the resonator by the hardware implant device.

25. The apparatus of claim 24, wherein the substrate is attached to the hardware implant device by an epoxy.

26. The apparatus of claim 24, wherein the hardware implant device includes a fracture fixation plate.

27. The apparatus of claim 24, wherein the substrate is flexible.

28. The apparatus of claim 27, wherein the flexible substrate is configured as a flexible tape.

29. The apparatus of claim 24, wherein the solid dielectric material is composed of silicon nitride and the conductive coil is composed of gold.

30. The apparatus of claim 24, wherein the resonator is composed of a metamaterial.

31. The apparatus of claim 24, wherein the conductive coil has one of a spiral, split-ring, or nested split-ring configuration.

32. The apparatus of claim 24, wherein the resonator is configured to have a resonant frequency ranging from 50 MHz to 7 GHz at no load.

33. A monitoring system comprising:
an apparatus implantable in a biological subject, the apparatus including a hardware implant device and a sensor device mounted to or integral with the hardware implant device,
wherein the sensor device comprises:
a substrate; and
a resonator configured as a strain gauge composed essentially of:
a solid dielectric material disposed over the substrate as a dielectric capacitor;
a conductive layer between the substrate and the solid dielectric material and in contact with the substrate and the solid dielectric material; and
at least one conductive coil disposed on the solid dielectric material,
wherein the substrate, the conductive layer, the solid dielectric material, and the conductive coil are configured to undergo strain as the hardware implant device mounted to or integral with the sensor device undergoes strain,
wherein the substrate, the conductive layer, the solid dielectric material, and the conductive coil are configured as a biocompatible sensor device for implantation in a biological subject, and
wherein the resonator is configured to be inductively powered without an incorporated power supply,
wherein the resonator is configured to reflect electromagnetic waves corresponding to a resonant frequency of the resonator in response to an alternating magnetic or electromagnetic field directed toward the sensor device, and
wherein the resonant frequency of the resonator shifts in correspondence with strain applied to the resonator by the hardware implant device;
an electromagnetic field generator configured to generate an alternating magnetic or electromagnetic field to power the resonator;
a receiver configured to receive electromagnetic waves reflected by the resonator in response to the resonator being excited by the generated alternating magnetic or electromagnetic field;
a device configured to determine a shift in a resonant frequency of the resonator based on the electromagnetic waves reflected by the resonator at different times over a period; and
an analyzer configured to determine a temporal change in strain of the hardware implant device based on the determined shift in the resonant frequency of the resonator over the period.

34. The monitoring system of claim 33, wherein the analyzer is configured to determine a change in the biological subject based on a temporal change in strain of the hardware implant device.

35. The monitoring system of claim 33, further including a machine-readable storage medium storing instructions executable by a processor of the monitoring system, for carrying out the instructions to:
determine the resonant frequency of the resonator;
determine the shift in the resonant frequency of the resonator based on the received reflected electromagnetic waves at different times over the period in response to electromagnetic probe signals directed toward the sensor device at different times over the period; and
determine the temporal change in strain of the hardware implant device based on the shift in resonant frequency of the resonator over the period.

36. The monitoring system of claim 35, wherein machine-readable medium includes instructions to store data of a strain-frequency calibration of the hardware implant device.

37. The monitoring system of claim 35, wherein machine-readable medium includes instructions to generate data representing fracture healing of the biological subject, the data based on the temporal changes in strain of the hardware implant device implanted in the biological subject relative to the fracture.

38. The monitoring system of claim 33, wherein the analyzer includes memory to store data of a strain-frequency calibration of the hardware implant device.

39. The monitoring system of claim 33, further including a memory device configured to store data representing fracture healing of the biological subject, the data being based on the temporal changes in strain of the hardware implant device implanted in the biological subject relative to the fracture.

40. A method of manufacturing an implantable device implantable in a subject, the method comprising the steps of:
fabricating a biocompatible sensor device that measures a change in strain the hardware implant device, and to be inductively powered without an integrated power supply; and
disposing the biocompatible sensor device on the hardware implant device,
wherein the fabricating step comprises the steps of:
providing a substrate; and
forming a resonator configured as a strain gauge by composed essentially of:
a conductive layer over the substrate in contact therewith;
a solid dielectric material on the conductive layer and in contact therewith as a dielectric capacitor; and
at least one conductive coil on the solid dielectric material, wherein the substrate, the conductive layer, the solid dielectric material, and the conductive coil are configured to undergo strain as the hardware implant device mounted to or integral with the sensor device undergoes strain, wherein the substrate, the conductive layer, the solid dielectric material, and the conductive coil are configured as a biocompatible sensor device for implantation in a biological subject, wherein the resonator is configured to reflect electromagnetic waves corresponding to a resonant frequency of the resonator in response to electromagnetic waves directed toward the sensor device, and wherein the resonant frequency of the resonator shifts in correspondence with strain applied to the resonator by the hardware implant device.

41. The method of claim 40, wherein the resonator is configured to have a resonant frequency ranging from 50 MHz to 7 GHz at no load.

* * * * *

UNITED STATES PATENT AND TRADEMARK OFFICE
CERTIFICATE OF CORRECTION

| | | |
|---|---|---|
| PATENT NO. | : 9,326,728 B2 | Page 1 of 1 |
| APPLICATION NO. | : 13/035662 | |
| DATED | : May 3, 2016 | |
| INVENTOR(S) | : Hilmi Volkan Demir et al. | |

It is certified that error appears in the above-identified patent and that said Letters Patent is hereby corrected as shown below:

On the title page
Item (56) References Cited, on page 2, column 2, lines 17, and 19-20, under Other Publications, in the citation of the article entitled "Bio-implantable passive on-chip RF-MEMS strain sensing resonators for orthopaedic applications", in the title, "passibe" should read --passive--, and the name of author "Ernie Unal" should read --Emre Unal--

In the claims
In column 30, line 60, the word "by" should be deleted. Column 30, line 60, should read: --forming a resonator configured as a strain gauge--

Signed and Sealed this
Twenty-sixth Day of July, 2016

Michelle K. Lee
*Director of the United States Patent and Trademark Office*